United States Patent
Zhu et al.

(10) Patent No.: US 8,420,869 B2
(45) Date of Patent: *Apr. 16, 2013

(54) PROCESS FOR THE PREPARATION OF 2,2,4,4-TETRAALKYLCYCLOBUTANE-1,3-DIOLS

(75) Inventors: Zhidong Zhu, Kingsport, TN (US); Gerald Charles Tustin, Kingsport, TN (US); Philip Conrad Heidt, Kingsport, TN (US); Zhufang Liu, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 201 days.

This patent is subject to a terminal disclaimer.

(21) Appl. No.: 12/963,698

(22) Filed: Dec. 9, 2010

(65) Prior Publication Data

US 2012/0149947 A1 Jun. 14, 2012

(51) Int. Cl.
  *C07C 29/145* (2006.01)
  *C07C 35/04* (2006.01)
(52) U.S. Cl.
  USPC .................................................. 568/839
(58) Field of Classification Search ............ 568/839
  See application file for complete search history.

(56) References Cited

U.S. PATENT DOCUMENTS

| | | | |
|---|---|---|---|
| 1,602,699 A | 10/1926 | Nightingale | |
| 2,160,841 A | 6/1939 | Dreyfus | |
| 2,202,046 A | 5/1940 | Dreyfus et al. | |
| 2,278,537 A | 4/1942 | Dreyfus et al. | |
| 2,720,507 A | 10/1955 | Caldwell | |
| 2,806,064 A | 9/1957 | McKlveen | |
| 2,901,466 A | 8/1959 | Kibler | |
| 2,936,324 A | 5/1960 | Hasek et al. | |
| 3,000,906 A | 9/1961 | Hasek et al. | |
| 3,030,335 A | 4/1962 | Goldberg | |
| 3,062,852 A | 11/1962 | Martin et al. | |
| 3,075,952 A | 1/1963 | Coover et al. | |
| 3,091,600 A | 5/1963 | Caldwell et al. | |
| 3,169,121 A | 2/1965 | Goldberg et al. | |
| 3,190,928 A | 6/1965 | Elam et al. | |
| 3,201,474 A | 8/1965 | Hasek et al. | |
| 3,207,814 A | 9/1965 | Goldberg et al. | |
| 3,218,372 A | 11/1965 | Okamura et al. | |
| 3,227,764 A | 1/1966 | Martin et al. | |
| 3,236,899 A | 2/1966 | Clark | |
| 3,249,652 A | 5/1966 | Quisenberry | |
| 3,259,469 A | 7/1966 | Painter et al. | |
| 3,287,390 A | 11/1966 | Poos et al. | |
| 3,288,854 A | 11/1966 | Martin | |
| 3,312,741 A | 4/1967 | Martin | |
| 3,313,777 A | 4/1967 | Elam et al. | |
| 3,317,466 A | 5/1967 | Caldwell et al. | |
| 3,329,722 A | 7/1967 | Rylander | |
| 3,360,547 A | 12/1967 | Wilson et al. | |
| 3,366,689 A | 1/1968 | Maeda et al. | |
| 3,386,935 A | 6/1968 | Jackson et al. | |
| 3,403,181 A | 9/1968 | Painter et al. | |
| T858012 I4 | 1/1969 | Caldwell et al. | |
| 3,484,339 A | 12/1969 | Caldwell | |
| 3,502,620 A | 3/1970 | Caldwell | |
| T873016 I4 | 4/1970 | Gilkey et al. | |
| 3,541,059 A | 11/1970 | Schaper | |
| 3,546,177 A | 12/1970 | Kibler et al. | |
| 3,629,202 A | 12/1971 | Gilkey et al. | |
| RE27,682 E | 6/1973 | Hermann et al. | |
| 3,772,405 A | 11/1973 | Hamb | |
| 3,799,953 A | 3/1974 | Freitag et al. | |
| 3,907,754 A | 9/1975 | Tershansy et al. | |
| 3,915,913 A | 10/1975 | Jackson, Jr. et al. | |
| 3,962,189 A | 6/1976 | Russin et al. | |
| 4,001,184 A | 1/1977 | Scott | |
| 4,010,145 A | 3/1977 | Russin et al. | |
| 4,046,933 A | 9/1977 | Stefanik | |
| 4,056,504 A | 11/1977 | Grundmeier et al. | |
| 4,084,889 A | 4/1978 | Vischer, Jr. | |
| 4,125,572 A | 11/1978 | Scott | |
| 4,156,069 A | 5/1979 | Prevorsek et al. | |
| 4,160,383 A | 7/1979 | Rauschenberger | |
| 4,185,009 A | 1/1980 | Idel et al. | |
| 4,188,314 A | 2/1980 | Fox et al. | |
| 4,194,038 A | 3/1980 | Baker et al. | |
| 4,263,364 A | 4/1981 | Seymour et al. | |
| 4,356,299 A | 10/1982 | Cholod et al. | |
| 4,367,186 A | 1/1983 | Adelmann et al. | |
| 4,379,802 A | 4/1983 | Weaver et al. | |

(Continued)

FOREIGN PATENT DOCUMENTS

BE 615850 4/1962
CA 2035149 8/1991

(Continued)

OTHER PUBLICATIONS

Abstract of U.S. Defense Publication T869,015, 869 O.G. 714, Dec. 16, 1969.
Abstract of U.S. Defense Publication T875,010, 875 O.G. 342, Jun. 9, 1970.
Chen et al., "The molecular basis for the relationship between the secondary relaxation and mechanical properties of a series of polyester copolymer glasses," Marcromolecules, 32:5944-5955 (1999).
Kelsey, E. et al., "High Impact, Amorphous Terephthalate Copolyesters of Rigid 2,2,4,4-Tetramethyl-1,3-cyclobutanediol with Flexible Diols," Macromolecules, vol. 33, 2000, pp. 5810-5818, American Chemical Society.
"Plastic Additives Handbook," 5$^{th}$ Edition, 2001, pp. 98-108 and pp. 109-112 (Hanser Gardner Publications, Inc., Cincinnati, OH.
Scheirs, John, et al., "Modern Polyesters: Chemistry and Technology of Polyesters and Copolyesters," Technology & Engineering, 2003, p. 287.

(Continued)

*Primary Examiner* — Brian J Davis
(74) *Attorney, Agent, or Firm* — Jennifer R. Knight; Eric D. Middlemas

(57) ABSTRACT

Disclosed is a process for the preparation of a 2,2,4,4-tetraalkylcyclobutane-1,3-diol by hydrogenation of the corresponding 2,2,4,4-tetraalkylcyclobutane-1,3-dione in the vapor phase in the presence of a supported catalyst. The process is useful for the preparation of 2,2,4,4-tetramethylcyclobutane-1,3-diol from 2,2,4,4-tetramethylcyclobutane-1,3-dione. The process can produce a 2,2,4,4-tetraalkylcyclobutane-1,3-diol product having a cis:trans isomer ratio of 1:1 or greater.

18 Claims, 1 Drawing Sheet

U.S. PATENT DOCUMENTS

| | | | |
|---|---|---|---|
| 4,384,106 A | 5/1983 | Go et al. |
| 4,391,954 A | 7/1983 | Scott |
| 4,424,140 A | 1/1984 | Weinberg et al. |
| 4,426,512 A | 1/1984 | Barbee et al. |
| 4,427,614 A | 1/1984 | Barham et al. |
| 4,430,484 A | 2/1984 | Quinn |
| 4,431,793 A | 2/1984 | Rosenquist |
| 4,452,933 A | 6/1984 | McCready |
| 4,465,820 A | 8/1984 | Miller et al. |
| 4,469,861 A | 9/1984 | Mark et al. |
| 4,480,086 A | 10/1984 | O'Neill |
| 4,525,504 A | 6/1985 | Morris et al. |
| 4,578,295 A | 3/1986 | Jabarin |
| 4,578,437 A | 3/1986 | Light et al. |
| 4,642,959 A | 2/1987 | Swiech, Jr. et al. |
| 4,738,880 A | 4/1988 | Asada et al. |
| 4,749,773 A | 6/1988 | Weaver et al. |
| 4,786,692 A | 11/1988 | Allen et al. |
| 4,816,308 A | 3/1989 | Shimizu et al. |
| 4,826,903 A | 5/1989 | Weaver et al. |
| 4,845,188 A | 7/1989 | Weaver et al. |
| 4,880,592 A | 11/1989 | Martini et al. |
| 4,882,412 A | 11/1989 | Weaver et al. |
| 4,892,922 A | 1/1990 | Weaver et al. |
| 4,892,923 A | 1/1990 | Weaver et al. |
| 4,937,134 A | 6/1990 | Schrenk et al. |
| 4,939,186 A | 7/1990 | Nelson et al. |
| 4,976,057 A | 12/1990 | Bianchi |
| 4,981,898 A | 1/1991 | Bassett |
| 4,985,342 A | 1/1991 | Muramoto et al. |
| 5,017,679 A | 5/1991 | Chang et al. |
| 5,017,680 A | 5/1991 | Sublett |
| 5,034,252 A | 7/1991 | Nilsson et al. |
| 5,104,450 A | 4/1992 | Sand et al. |
| 5,118,760 A | 6/1992 | Blakely et al. |
| 5,118,847 A | 6/1992 | Jackson et al. |
| 5,142,088 A | 8/1992 | Phelps et al. |
| 5,169,994 A | 12/1992 | Sumner, Jr. et al. |
| 5,183,863 A | 2/1993 | Nakamura et al. |
| 5,191,038 A | 3/1993 | Krabbenhoft et al. |
| 5,207,967 A | 5/1993 | Small et al. |
| 5,219,510 A | 6/1993 | Machell et al. |
| 5,224,958 A | 7/1993 | Warunek et al. |
| 5,239,020 A | 8/1993 | Morris |
| 5,256,761 A | 10/1993 | Blount, Jr. |
| 5,258,556 A | 11/1993 | Sumner, Jr. et al. |
| 5,268,219 A | 12/1993 | Harada et al. |
| 5,288,715 A | 2/1994 | Machell et al. |
| 5,288,764 A | 2/1994 | Rotter et al. |
| 5,292,783 A | 3/1994 | Buchanan et al. |
| 5,310,611 A | 5/1994 | Okabe et al. |
| 5,310,787 A | 5/1994 | Kutsuwa et al. |
| 5,326,584 A | 7/1994 | Kamel et al. |
| 5,326,821 A | 7/1994 | Sasaki et al. |
| 5,331,034 A | 7/1994 | Pfahler et al. |
| 5,333,073 A | 7/1994 | Suzuki |
| 5,354,791 A | 10/1994 | Gallucci |
| 5,372,864 A | 12/1994 | Weaver et al. |
| 5,372,879 A | 12/1994 | Handa et al. |
| 5,378,796 A | 1/1995 | George et al. |
| 5,382,292 A | 1/1995 | Conroy et al. |
| 5,384,377 A | 1/1995 | Weaver et al. |
| 5,475,144 A | 12/1995 | Watson et al. |
| 5,480,926 A | 1/1996 | Fagerburg et al. |
| 5,486,562 A | 1/1996 | Borman et al. |
| 5,489,665 A | 2/1996 | Yamato et al. |
| 5,494,992 A | 2/1996 | Kanno et al. |
| 5,498,668 A | 3/1996 | Scott |
| 5,498,688 A | 3/1996 | Oshino et al. |
| 5,506,014 A | 4/1996 | Minnick |
| 5,523,382 A | 6/1996 | Beavers et al. |
| 5,534,609 A | 7/1996 | Lewis et al. |
| 5,552,512 A | 9/1996 | Sublett |
| 5,591,530 A | 1/1997 | Warner et al. |
| 5,633,340 A | 5/1997 | Hoffman et al. |
| 5,650,453 A | 7/1997 | Eckberg et al. |
| 5,654,347 A | 8/1997 | Khemani et al. |
| 5,656,715 A | 8/1997 | Dickerson et al. |
| 5,668,243 A | 9/1997 | Yau et al. |
| 5,681,918 A | 10/1997 | Adams et al. |
| 5,688,874 A | 11/1997 | Hoffman |
| 5,696,176 A | 12/1997 | Khemani et al. |
| 5,705,575 A | 1/1998 | Kelsey |
| 5,783,307 A | 7/1998 | Fagerburg et al. |
| 5,804,617 A | 9/1998 | Hoffman et al. |
| 5,814,679 A | 9/1998 | Eckberg et al. |
| 5,859,116 A | 1/1999 | Shih |
| 5,863,622 A | 1/1999 | Jester |
| 5,902,631 A | 5/1999 | Wang et al. |
| 5,907,026 A | 5/1999 | Factor et al. |
| 5,942,585 A | 8/1999 | Scott et al. |
| 5,955,565 A | 9/1999 | Morris et al. |
| 5,958,539 A | 9/1999 | Eckart et al. |
| 5,958,581 A | 9/1999 | Khanarian et al. |
| 5,959,066 A | 9/1999 | Charbonneau et al. |
| 5,962,625 A | 10/1999 | Yau |
| 5,977,347 A | 11/1999 | Shuto et al. |
| 5,989,663 A | 11/1999 | Morris et al. |
| 6,001,910 A | 12/1999 | Blumenthal et al. |
| 6,005,059 A | 12/1999 | Scott et al. |
| 6,011,124 A | 1/2000 | Scott et al. |
| 6,012,597 A | 1/2000 | Nishihara et al. |
| 6,022,603 A | 2/2000 | Umeda et al. |
| 6,025,061 A | 2/2000 | Khanarian et al. |
| 6,030,671 A | 2/2000 | Yang et al. |
| 6,037,424 A | 3/2000 | Scott et al. |
| 6,043,322 A | 3/2000 | Scott et al. |
| 6,044,996 A | 4/2000 | Carew et al. |
| 6,063,464 A | 5/2000 | Charbonneau et al. |
| 6,063,465 A | 5/2000 | Charbonneau et al. |
| 6,063,495 A | 5/2000 | Charbonneau et al. |
| 6,084,019 A | 7/2000 | Matayabas et al. |
| 6,096,854 A | 8/2000 | Morris et al. |
| 6,114,575 A | 9/2000 | McMahon et al. |
| 6,120,477 A | 9/2000 | Campbell et al. |
| 6,120,889 A | 9/2000 | Turner et al. |
| 6,126,992 A | 10/2000 | Khanarian et al. |
| 6,127,492 A | 10/2000 | Nagashima et al. |
| 6,146,228 A | 11/2000 | Mougin et al. |
| 6,150,494 A | 11/2000 | Wang et al. |
| 6,183,848 B1 | 2/2001 | Turner et al. |
| 6,191,209 B1 | 2/2001 | Andrews et al. |
| 6,211,309 B1 | 4/2001 | McIntosh et al. |
| 6,221,556 B1 | 4/2001 | Gallucci et al. |
| 6,225,436 B1 | 5/2001 | Eiffler et al. |
| 6,232,504 B1 | 5/2001 | Barteau et al. |
| 6,239,210 B1 | 5/2001 | Kim et al. |
| 6,255,523 B1 | 7/2001 | Panandiker et al. |
| 6,287,656 B1 | 9/2001 | Turner et al. |
| 6,307,006 B1 | 10/2001 | Konig et al. |
| 6,309,718 B1 | 10/2001 | Sprayberry |
| 6,320,042 B1 | 11/2001 | Michihata et al. |
| 6,323,291 B1 | 11/2001 | Mason et al. |
| 6,323,304 B1 | 11/2001 | Lemmon et al. |
| 6,342,304 B1 | 1/2002 | Buchanan et al. |
| 6,352,783 B1 | 3/2002 | Fagerburg |
| 6,354,986 B1 | 3/2002 | Hlavinka et al. |
| 6,359,070 B1 | 3/2002 | Khanarian et al. |
| 6,406,792 B1 | 6/2002 | Briquet et al. |
| 6,437,083 B1 | 8/2002 | Brack et al. |
| 6,448,334 B1 | 9/2002 | Verhoogt et al. |
| 6,458,468 B1 | 10/2002 | Moskala et al. |
| 6,504,002 B1 | 1/2003 | Karlik et al. |
| 6,559,272 B1 | 5/2003 | Jeon et al. |
| 6,573,328 B2 | 6/2003 | Kropp et al. |
| 6,599,994 B2 | 7/2003 | Shelby et al. |
| 6,600,080 B1 | 7/2003 | Nagamura et al. |
| 6,639,067 B1 | 10/2003 | Brinegar et al. |
| 6,656,577 B1 | 12/2003 | Adelman et al. |
| 6,669,980 B2 | 12/2003 | Hansen |
| 6,723,768 B2 | 4/2004 | Adams et al. |
| 6,733,716 B2 | 5/2004 | Belcher |
| 6,740,377 B2 | 5/2004 | Pecorini et al. |
| 6,773,653 B2 | 8/2004 | Miller et al. |
| 6,818,293 B1 | 11/2004 | Keep et al. |
| 6,818,730 B2 | 11/2004 | Brandenburg et al. |
| 6,846,440 B2 | 1/2005 | Flynn et al. |

| | | |
|---|---|---|
| 6,846,508 B1 | 1/2005 | Colas et al. |
| 6,896,966 B2 | 5/2005 | Crawford et al. |
| 6,908,650 B2 | 6/2005 | Odorisio et al. |
| 6,914,120 B2 | 7/2005 | Germroth et al. |
| 6,919,489 B1 | 7/2005 | McCusker-Orth |
| 7,037,576 B2 | 5/2006 | Willham et al. |
| 7,048,978 B2 | 5/2006 | Tanaka et al. |
| 7,053,143 B2 | 5/2006 | Mori et al. |
| 7,122,661 B2 | 10/2006 | Fleche et al. |
| 7,169,880 B2 | 1/2007 | Shelby et al. |
| 7,297,755 B2 | 11/2007 | Shelby et al. |
| 7,354,628 B2 | 4/2008 | Steube |
| 7,375,154 B2 | 5/2008 | Stafford et al. |
| 7,427,430 B2 | 9/2008 | Rhee et al. |
| 7,468,409 B2 | 12/2008 | Pearson et al. |
| 7,482,397 B2 | 1/2009 | Pearson et al. |
| 2001/0029324 A1 | 10/2001 | Walker et al. |
| 2001/0031805 A1 | 10/2001 | Buhler |
| 2001/0034419 A1 | 10/2001 | Kanayama et al. |
| 2001/0044003 A1 | 11/2001 | Galluci et al. |
| 2002/0055586 A1 | 5/2002 | Dalgewicz, III et al. |
| 2002/0128357 A1 | 9/2002 | Goossens et al. |
| 2002/0132963 A1 | 9/2002 | Quillen |
| 2002/0137856 A1 | 9/2002 | Andrews et al. |
| 2002/0188092 A1 | 12/2002 | Moskala et al. |
| 2002/0198297 A1 | 12/2002 | Odorisio et al. |
| 2003/0032737 A1 | 2/2003 | Andrews et al. |
| 2003/0060546 A1 | 3/2003 | Moskala et al. |
| 2003/0075516 A1 | 4/2003 | Rothman et al. |
| 2003/0077546 A1 | 4/2003 | Donovan et al. |
| 2003/0135015 A1 | 7/2003 | Fujimaki et al. |
| 2003/0139497 A1 | 7/2003 | Odorisio et al. |
| 2003/0149177 A1 | 8/2003 | Andrews et al. |
| 2003/0169514 A1 | 9/2003 | Bourdelais et al. |
| 2003/0187151 A1 | 10/2003 | Adams et al. |
| 2003/0195295 A1 | 10/2003 | Mahood et al. |
| 2003/0221716 A1 | 12/2003 | Olson |
| 2003/0229181 A1 | 12/2003 | Hariharan et al. |
| 2004/0022526 A1 | 2/2004 | Kuno et al. |
| 2004/0063864 A1 | 4/2004 | Adams et al. |
| 2004/0101687 A1 | 5/2004 | Crawford et al. |
| 2004/0106707 A1 | 6/2004 | Su et al. |
| 2004/0106767 A1 | 6/2004 | Simon et al. |
| 2004/0108623 A1 | 6/2004 | Deeter et al. |
| 2004/0138381 A1 | 7/2004 | Blasius et al. |
| 2004/0145700 A1 | 7/2004 | Miniutti et al. |
| 2004/0164279 A1 | 8/2004 | Stevenson et al. |
| 2004/0202822 A1 | 10/2004 | Bourdelais et al. |
| 2004/0214984 A1 | 10/2004 | Keep et al. |
| 2005/0008885 A1 | 1/2005 | Blakely et al. |
| 2005/0072060 A1 | 4/2005 | Moncho et al. |
| 2005/0075466 A1 | 4/2005 | Oguro et al. |
| 2005/0096453 A1 | 5/2005 | Flynn et al. |
| 2005/0101759 A1 | 5/2005 | Odorisio et al. |
| 2005/0113556 A1 | 5/2005 | Strand et al. |
| 2005/0119359 A1 | 6/2005 | Shelby et al. |
| 2005/0124779 A1 | 6/2005 | Shelby et al. |
| 2005/0181155 A1 | 8/2005 | Share et al. |
| 2005/0209435 A1 | 9/2005 | Hirokane et al. |
| 2006/0004151 A1 | 1/2006 | Shaikh et al. |
| 2006/0036012 A1 | 2/2006 | Hayes et al. |
| 2006/0094858 A1 | 5/2006 | Turner et al. |
| 2006/0111481 A1 | 5/2006 | Pearson et al. |
| 2006/0111519 A1 | 5/2006 | Strand et al. |
| 2006/0135668 A1 | 6/2006 | Hayes |
| 2006/0146228 A1 | 7/2006 | Sogo et al. |
| 2006/0151907 A1 | 7/2006 | Kashiwabara |
| 2006/0180560 A1 | 8/2006 | Robinson |
| 2006/0197246 A1 | 9/2006 | Hale et al. |
| 2006/0199904 A1 | 9/2006 | Hale et al. |
| 2006/0199919 A1 | 9/2006 | Hale et al. |
| 2006/0228507 A1 | 10/2006 | Hale et al. |
| 2006/0234073 A1 | 10/2006 | Hale et al. |
| 2006/0235167 A1 | 10/2006 | Hale et al. |
| 2006/0241325 A1 | 10/2006 | Komplin et al. |
| 2006/0247388 A1 | 11/2006 | Hale et al. |
| 2006/0270773 A1 | 11/2006 | Hale et al. |
| 2006/0270806 A1 | 11/2006 | Hale |
| 2007/0049667 A1 | 3/2007 | Kim et al. |
| 2007/0071930 A1 | 3/2007 | Shelby et al. |
| 2008/0132738 A1 | 6/2008 | McCusker-Orth et al. |
| 2008/0154069 A1 | 6/2008 | McCusker-Orth et al. |
| 2008/0201910 A1 | 8/2008 | O'Meadhra et al. |
| 2009/0123756 A1 | 5/2009 | Hashimoto et al. |

FOREIGN PATENT DOCUMENTS

| | | |
|---|---|---|
| DE | 29 21 868 A1 | 12/1980 |
| DE | 197 27 709 | 6/1997 |
| DE | 198 11 773 A1 | 9/1999 |
| EP | 0 039 838 A1 | 11/1981 |
| EP | 0 273 144 | 5/1987 |
| EP | 0 282 277 | 9/1988 |
| EP | 0 372 846 | 6/1990 |
| EP | 0 544 008 A1 | 6/1993 |
| EP | 0 595 413 A1 | 5/1994 |
| EP | 0 698 631 | 2/1996 |
| EP | 0 714 764 A2 | 6/1996 |
| EP | 0 902 052 A1 | 3/1999 |
| EP | 0 930 531 A1 | 7/1999 |
| EP | 1 035 167 A | 9/2000 |
| EP | 1 066 825 A1 | 1/2001 |
| EP | 1 674 496 A1 | 6/2006 |
| FR | 1278284 | 12/1961 |
| FR | 1291273 | 5/1965 |
| FR | 1432471 | 2/1966 |
| FR | 1434658 | 2/1966 |
| FR | 2112400 | 6/1972 |
| GB | 962913 | 7/1964 |
| GB | 1041651 | 9/1966 |
| GB | 1044015 | 9/1966 |
| GB | 1047043 | 11/1966 |
| GB | 1090241 | 11/1967 |
| GB | 1130558 | 10/1968 |
| GB | 1 278 284 | 6/1972 |
| GB | 1364732 | 8/1974 |
| GB | 2216919 A | 10/1989 |
| JP | 56-88440 A | 12/1979 |
| JP | 03207743 | 9/1991 |
| JP | 65-01040 | 2/1994 |
| JP | 9-59371 A | 4/1997 |
| JP | 11-222516 | 8/1999 |
| JP | 2001-066701 | 8/1999 |
| JP | 2000-352620 A | 12/2000 |
| JP | 2001-098086 | 4/2001 |
| JP | 2001-214049 | 8/2001 |
| JP | 2003292593 A | 10/2003 |
| JP | 2004-058565 A | 2/2004 |
| JP | 2004-066624 A | 3/2004 |
| JP | 2004-067973 A | 3/2004 |
| JP | 2004-244497 A | 9/2004 |
| JP | 2004-292558 A | 10/2004 |
| JP | 2005-254757 A | 9/2005 |
| JP | 2007-069914 A | 3/2007 |
| JP | 2007-253491 A | 10/2007 |
| KR | 2001-089942 | 10/2001 |
| KR | 2003-054611 | 7/2003 |
| WO | WO 97-01118 | 1/1997 |
| WO | WO 01-06981 | 2/2001 |
| WO | WO 01-85824 A2 | 11/2001 |
| WO | WO 02-055570 A1 | 7/2002 |
| WO | WO 02-059207 | 8/2002 |
| WO | WO2004-009146 A1 | 1/2004 |
| WO | WO 2004-039860 | 5/2004 |
| WO | WO 2004-104077 A1 | 12/2004 |
| WO | WO 2004-106988 A2 | 12/2004 |
| WO | WO 2005-007735 A2 | 1/2005 |
| WO | WO 2005-026241 A1 | 3/2005 |
| WO | WO 2006-025827 | 3/2006 |
| WO | WO 2006-127755 A2 | 11/2006 |
| WO | WO 2006-127831 A1 | 11/2006 |
| WO | WO 2007-053434 A1 | 5/2007 |
| WO | WO 2007-053548 A2 | 5/2007 |
| WO | WO 2007-053549 A1 | 5/2007 |
| WO | WO 2007/123631 A | 11/2007 |

OTHER PUBLICATIONS

English language Abstract of JP 02-305816 from Patent Abstracts of Japan, Dec. 19, 1990.

English language translation of Belgian Patent No. BE 615,850, Apr. 13, 1962.
English language translation of French Patent No. FR 1,432,471, Feb. 7, 1966.
English language translation of French Patent No. FR 1,434,658, Feb. 28, 1966.
U.S. Appl. No. 11/390,555, filed Mar. 28, 2006, Emmett Dudley Crawford, et al.
U.S. Appl. No. 11/390,563, filed Mar. 28, 2006, Emmett Dudley Crawford, et al.
U.S. Appl. No. 11/390,629, filed Mar. 28, 2006, Emmett Dudley Crawford, et al.
U.S. Appl. No. 11/390,630, filed Mar. 28, 2006, Emmett Dudley Crawford, et al.
U.S. Appl. No. 11/390,631, filed Mar. 28, 2006, Emmett Dudley Crawford, et al.
U.S. Appl. No. 11/390,654, filed Mar. 28, 2006, Emmett Dudley Crawford, et al.
U.S. Appl. No. 11/390,655, filed Mar. 28, 2006, Emmett Dudley Crawford, et al.
U.S. Appl. No. 11/390,671, filed Mar. 28, 2006, Emmett Dudley Crawford, et al.
U.S. Appl. No. 11/390,672, filed Mar. 28, 2006, Emmett Dudley Crawford, et al.
U.S. Appl. No. 11/390,722, filed Mar. 28, 2006, Emmett Dudley Crawford, et al.
U.S. Appl. No. 11/390,750, filed Mar. 28, 2006, Emmett Dudley Crawford, et al.
U.S. Appl. No. 11/390,751, filed Mar. 28, 2006, Emmett Dudley Crawford, et al.
U.S. Appl. No. 11/390,752, filed Mar. 28, 2006, Emmett Dudley Crawford, et al.
U.S. Appl. No. 11/390,773, filed Mar. 28, 2006, Emmett Dudley Crawford, et al.
U.S. Appl. No. 11/390,793, filed Mar. 28, 2006, Emmett Dudley Crawford, et al.
U.S. Appl. No. 11/390,794, filed Mar. 28, 2006, Emmett Dudley Crawford, et al.
U.S. Appl. No. 11/390,809, filed Mar. 28, 2006, Wesley Raymond Hale, et al.
U.S. Appl. No. 11/390,811, filed Mar. 28, 2006, Emmett Dudley Crawford, et al.
U.S. Appl. No. 11/390,812, filed Mar. 28, 2006, Wesley Raymond Hale, et al.
U.S. Appl. No. 11/390,814, filed Mar. 28, 2006, Emmett Dudley Crawford, et al.
U.S. Appl. No. 11/390,826, filed Mar. 28, 2006, Emmett Dudley Crawford, et al.
U.S. Appl. No. 11/390,827, filed Mar. 28, 2006, Emmett Dudley Crawford, et al.
U.S. Appl. No. 11/390,836, filed Mar. 28, 2006, Emmett Dudley Crawford, et al.
U.S. Appl. No. 11/390,846, filed Mar. 28, 2006, Wesley Raymond Hale, et al.
U.S. Appl. No. 11/390,847, filed Mar. 28, 2006, Emmett Dudley Crawford, et al.
U.S. Appl. No. 11/390,853, filed Mar. 28, 2006, Emmett Dudley Crawford, et al.
U.S. Appl. No. 11/390,858, filed Mar. 28, 2006, Emmett Dudley Crawford, et al.
U.S. Appl. No. 11/390,864, filed Mar. 28, 2006, Wesley Raymond Hale, et al.
U.S. Appl. No. 11/390,865, filed Mar. 28, 2006, Emmett Dudley Crawford, et al.
U.S. Appl. No. 11/390,882, filed Mar. 28, 2006, Emmett Dudley Crawford, et al.
U.S. Appl. No. 11/390,883, filed Mar. 28, 2006, Thomas Joseph Pecorini, et al.
U.S. Appl. No. 11/390,908, filed Mar. 28, 2006, Wesley Raymond Hale, et al.
U.S. Appl. No. 11/391,063, filed Mar. 28, 2006, Emmett Dudley Crawford, et al.
U.S. Appl. No. 11/391,124, filed Mar. 28, 2006, Wesley Raymond Hale, et al.
U.S. Appl. No. 11/391,125, filed Mar. 28, 2006, Emmett Dudley Crawford, et al.
U.S. Appl. No. 11/391,137, filed Mar. 28, 2006, Emmett Dudley Crawford, et al.
U.S. Appl. No. 11/391,156, filed Mar. 28, 2006, Emmett Dudley Crawford, et al.
U.S. Appl. No. 11/391,485, filed Mar. 28, 2006, Emmett Dudley Crawford, et al.
U.S. Appl. No. 11/391,495, filed Mar. 28, 2006, Emmett Dudley Crawford, et al.
U.S. Appl. No. 11/391,505, filed Mar. 28, 2006, Emmett Dudley Crawford, et al.
U.S. Appl. No. 11/391,565, filed Mar. 28, 2006, Emmett Dudley Crawford, et al.
U.S. Appl. No. 11/391,571, filed Mar. 28, 2006, Emmett Dudley Crawford, et al.
U.S. Appl. No. 11/391,576, filed Mar. 28, 2006, Emmett Dudley Crawford, et al.
U.S. Appl. No. 11/391,642, filed Mar. 28, 2006, Emmett Dudley Crawford, et al.
U.S. Appl. No. 11/391,659, filed Mar. 28, 2006, Emmett Dudley Crawford, et al.
U.S. Appl. No. 11/588,524, filed Oct. 27, 2006, Emmett Dudley Crawford, et al.
U.S. Appl. No. 11/588,458, filed Oct. 27, 2006, Emmett Dudley Crawford, et al.
U.S. Appl. No. 11/588,907, filed Oct. 27, 2006, Emmett Dudley Crawford, et al.
U.S. Appl. No. 11/588,527, filed Oct. 27, 2006, Emmett Dudley Crawford, et al.
U.S. Appl. No. 11/588,906, filed Oct. 27, 2006, Ted Calvin Germroth, et al.
U.S. Appl. No. 11/588,883, filed Oct. 27, 2006, Ted Calvin Germroth, et al.
U.S. Appl. No. 11/588,554, filed Oct. 27, 2006, Emmett Dudley Crawford, et al.
U.S. Appl. No. 11/635,434, filed Dec. 7, 2006, Emmett Dudley Crawford.
U.S. Appl. No. 11/635,433, filed Dec. 7, 2006, Emmett Dudley Crawford.
U.S. Appl. No. 11/439,062, filed May 23, 2006, Wesley Raymond Hale, et al.
U.S. Appl. No. 11/439,340, filed May 23, 2006, Wesley Raymond Hale.
U.S. Appl. No. 11/706,476, filed Feb. 14, 2007, Leslie Shane Moody, et al.
U.S. Appl. No. 11/706,791, filed Feb. 14, 2007, Leslie Shane Moody, et al.
U.S. Appl. No. 12/091,568, filed Apr. 25, 2008, Emmett Dudley Crawford, et al.
U.S. Appl. No. 12/091,566, filed Apr. 25, 2008, Emmett Dudley Crawford, et al.
U.S. Appl. No. 12/091,570, filed Apr. 25, 2008, Ted Calvin Germroth, et al.
U.S. Appl. No. 12/091,572, filed Apr. 25, 2008, Ted Calvin Germroth, et al.
U.S. Appl. No. 12/294,690, filed Sep. 26, 2008, Ted Calvin Germroth et al.
U.S. Appl. No. 12/294,686, filed Sep. 26, 2008, Ted Calvin Germroth et al.
U.S. Appl. No. 12/274,692, filed Nov. 20, 2008, Thomas Joseph Pecorini et al.
U.S. Appl. No. 12/338,453, filed Dec. 18, 2008, Emmett Dudley Crawford, et al.
U.S. Appl. No. 12/361,779, filed Jan. 29, 2009, Emmett Dudley Crawford.
U.S. Appl. No. 12/365,515, filed Feb. 4, 2009, Emmett Dudley Crawford.
Chapter 4—*Processing of Plastics* in "*Plastics Engineering, 3$^{rd}$ ed*", R.J. Crawford, Butterworth-Heinemann Publisher, 1998, Oxford, England, pp. 245-342.

Fox equation (T.G. Fox, Session J, Bull. Am. Phys. Soc., 1, 123 (1956)).

*The Technology of Plasticizers*, by J. Kern Sears and Joseph R Darby, published by Society of Plastic Engineers-Wiley and Sons, New York, 1982; pp. 136-139.

Coleman et al., "Polymer Reviews—A Practical Guide to Polymer Miscibility," *Polymer 31*, pp. 1187-1203 (1990).

"*Hansen Solubility Parameters, a Users Handbook*", by Charles M. Hansen, Chapter 1, CRC Press, 2000, pp. 1-24.

Martinez et al., "*Phase Behavior and Mechanical Properties of Injection Molded Poly (Ethylene Terephthalate )—Polyarylate Blends*"; Journal of Applied Polymer Science, John Wiley and Sons Inc. New York, US, vol. 45, No. 7, Jul. 5, 1992, p. 1135-1143.

Won Ho Jo et al. : :*Miscibility of poly(ether imide)-poly(ethylene terephthalate) blends*; Polymer Bulletin, Springer, Heidelberg, DE, vol. 33, No. 1, Jun. 1, 1994, p. 113-118 (1994).

Anonymous: "*Poly (ethylene naphthalenedicarboxylate)-polyetherimide blends*" Research Disclosure, Mason Publications, Hampshire, GB, vol. 283, No. 38, Nov. 1987.

ASTM D1525-06, *Standard Test Method for Vicat Softening Temperature of Plastics*, Mar. 15, 2006.

ASTM D648-06, *Standard Test Method for Deflection Temperature of Plastics Under Flexural Load in the Edgewise Position*, Mar. 15, 2006.

ASTM D256-06, *Standard Test Methods for Determining the Izod Pendulum Impact Resistance of Plastics*, Mar. 15, 2006.

ASTM D790-03, *Standard Test Methods for Flexural Properties of Unreinforced and Reinforced Plastics and Electrical Insulating Materials*, Mar. 10, 2003.

ASTM D638-03, *Standard Test Method for Tensile Properties of Plastics*, Dec. 1, 2003.

ASTM D3418-03, *Transition Temperatures and Enthalpies of Fusion and Crystallization of Polymers by Differential Scanning Calorimetry*, Dec. 1, 2003.

Database WPI, Section Ch, Week 200536, Derwent Publications Ltd., London, GB; Class A23, AN 2005-355258, XP002396922 & WO 2005-030833 A1 (Kanebo Ltd) Apr. 7, 2005 abstract.

Shearer, N.H., "T18-Type 1 Polyesters," Mar. 1966, SPE Annual Technical Conference and Exhibition, XP009080224.

Gachter, Muller, "Taschenbuch der Kunststoff-Additive," 1990, Carl Hanser Verlag Munchen Wien, XP02450422, pp. 96-97.

Gachter, Muller, "Kunstoff-Additive," 1990, Carl Hanser Verlag Munchen Wien, XP 02449987, pp. 96-99.

Brown, R., "Taschenbuch Kunstoff-Additive", 1990, Carl Hanswer Verlag Munchen Wiel, XP002455247, pp. 361-363.

Chang, S. et al., "Effect of Stabilizers on the Preparation of Poly(ethylene Terephthalate)", Journal of Polymer Science, Polymer Chemistry Edition, 1982, vol. 20, pp. 2053-2061, John Wiley & Sons, Inc.

USPTO Office Action dated Mar. 11, 2008 for copending U.S. Appl. No. 11/391,642.

USPTO Office Action dated Mar. 24, 2008 for copending U.S. Appl. No. 11/390,908.

USPTO Office Action dated Apr. 15, 2008 for copending U.S. Appl. No. 11/390,629.

USPTO Office Action dated Apr. 16, 2008 for copending U.S. Appl. No. 11/390,751.

USPTO Office Action dated Apr. 17, 2008 for copending U.S. Appl. No. 11/390,814.

USPTO Office Action dated Jun. 3, 2008 for copending U.S. Appl. No. 11/391,063.

USPTO Office Action dated Sep. 10, 2008 for copending U.S. Appl. No. 11/390,752.

USPTO Office Action dated Sep. 10, 2008 for copending U.S. Appl. No. 11/390,794.

USPTO Office Action dated Sep. 19, 2008 for copending U.S. Appl. No. 11/391,565.

USPTO Office Action dated Oct. 2, 2008 for copending U.S. Appl. No. 11/390,671.

USPTO Office Action dated Sep. 24, 2008 for copending U.S. Appl. No. 11/390,631.

USPTO Office Action dated Oct. 1, 2008 for copending U.S. Appl. No. 11/390,655.

USPTO Office Action dated Sep. 29, 2008, for copending U.S. Appl. No. 11/391,137.

USPTO Office Action dated Sep. 9, 2008 for copending U.S. Appl. No. 11/391,571.

USPTO Office Action dated Oct. 22, 2008 for copending U.S. Appl. No. 11/391,125.

USPTO Office Action dated Oct. 20, 2008 for copending U.S. Appl. No. 11/390,672.

USPTO Office Action dated Oct. 8, 2008 for copending U.S. Appl. No. 11/390,853.

USPTO Office Action dated Oct. 9, 2008 for copending U.S. Appl. No. 11/391,505.

USPTO Notice of Allowance dated Oct. 7, 2008 for copending U.S. Appl. No. 11/390,908.

USPTO Office Action dated Oct. 14, 2008 for copending U.S. Appl. No. 11/390,811.

USPTO Office Action dated Oct. 22, 2008 for copending U.S. Appl. No. 11/390,750.

USPTO Office Action dated Oct. 22, 2008 for copending U.S. Appl. No. 11/390,865.

USPTO Office Action dated Oct. 14, 2008 for copending U.S. Appl. No. 11/390,654.

USPTO Office Action dated Oct. 20, 2008 for copending U.S. Appl. No. 11/390,836.

Copending application, U.S. Appl. No. 12/254,894, filed on Oct. 21, 2008, Gary Michael Stack, et al.

Copending Application U.S. Appl. No. 12/390,694, filed on Feb. 23, 2009, Gary Michael Stack.

USPTO Office Action dated Oct. 29, 2008 for copending U.S. Appl. No. 11/390-955.

USPTO Notice of Allowance dated Nov. 3, 2008 for copending U.S. Appl. No. 11/391,642.

USPTO Office Action dated Nov. 3, 2008 for copending U.S. Appl. No. 11/391,485.

USPTO Office Action dated Oct. 29, 2008 for copending U.S. Appl. No. 11/390,864.

USPTO Office Action dated Oct. 30, 2008 for copending U.S. Appl. No. 11/391,495.

USPTO Office Action dated Oct. 31, 2008 for copending U.S. Appl. No. 11/391,156.

USPTO Office Action dated Nov. 3, 2008 for copending U.S. Appl. No. 11/390,883.

USPTO Office Action dated Dec. 19, 2008 for copending U.S. Appl. No. 11/390,751.

USPTO Office Action dated Dec. 31, 2008 for copending U.S. Appl. No. 11/390,827.

USPTO Office Action dated Dec. 31, 2008 for copending U.S. Appl. No. 11/390,826.

USPTO Office Action dated Nov. 14, 2008 for copending U.S. Appl. No. 11/390,630.

USPTO Office Action dated Dec. 19, 2008 for copending U.S. Appl. No. 11/391,576.

USPTO Office Action dated Dec. 19, 2008 for copending U.S. Appl. No. 11/390,629.

USPTO Office Action dated Dec. 31, 2008 for copending U.S. Appl. No. 11/390,773.

USPTO Office Action dated Dec. 12, 2008 for copending U.S. Appl. No. 11/391,063.

USPTO Office Action dated Dec. 19, 2008 for copending U.S. Appl. No. 11/390,814.

USPTO Office Action dated Dec. 31, 2008 for copending U.S. Appl. No. 11/390,722.

USPTO Office Action dated Nov. 14, 2008 for copending U.S. Appl. No. 11/390,882.

USPTO Office Action dated Jan. 29, 2009 for copending U.S. Appl. No. 11/588,524.

USPTO Office Action dated Jan. 30, 2009 for copending U.S. Appl. No. 11/588,458.

USPTO Office Action dated Feb. 2, 2009 for copending U.S. Appl. No. 11/390,853.

USPTO Office Action dated Jan. 21, 2009 for copending U.S. Appl. No. 11/390,847.

USPTO Office Action dated Jan. 12, 2009 for copending U.S. Appl. No. 11/390,858.
USPTO Office Action dated Jan. 26, 2009 for copending U.S. Appl. No. 11/391,659.
USPTO Office Action dated Jan. 26, 2009 for copending U.S. Appl. No. 11/588,554.
USPTO Office Action dated Feb. 3, 2009 for copending U.S. Appl. No. 11/391,505.
USPTO Office Action dated Feb. 10, 2009 for copending U.S. Appl. No. 11/390,865.
USPTO Office Action dated Feb. 12, 2009 for copending U.S. Appl. No. 11/439,062.
USPTO Office Action dated Feb. 13, 2009 for copending U.S. Appl. No. 11/439,340.
USPTO Office Action dated Feb. 25, 2009 for copending U.S. Appl. No. 11/588,907.
USPTO Office Action dated Feb. 25, 2009 for copending U.S. Appl. No. 11/588,527.
USPTO Office Action dated Feb. 27, 2009 for copending U.S. Appl. No. 11/390,955.
USPTO Office Action dated Feb. 25, 2009 for copending U.S. Appl. No. 11/588,906.
USPTO Office Action dated Feb. 25, 2009 for copending U.S. Appl. No. 11/588,883.
USPTO Office Action dated Mar. 5, 2009 for copending U.S. Appl. No. 11/390,864.
USPTO Office Action dated Mar. 6, 2009 for copending U.S. Appl. No. 11/391,156.
USPTO Office Action dated Feb. 25, 2009 for copending U.S. Appl. No. 11/390,811.
USPTO Office Action dated Feb. 27, 2009 for copending U.S. Appl. No. 11/390,654.
USPTO Office Action dated Feb. 27, 2009 for copending U.S. Appl. No. 11/390,836.
USPTO Office Action dated Mar. 13, 2009 for copending U.S. Appl. No. 11/390,883.
USPTO Office Action dated Mar. 11, 2009 for copending U.S. Appl. No. 11/390,630.
USPTO Office Action dated Mar. 9, 2009 for copending U.S. Appl. No. 11/391,495.
USPTO Office Action dated Mar. 9, 2009 for copending U.S. Appl. No. 11/390,750.
USPTO Office Action dated Mar. 16, 2009 for copending U.S. Appl. No. 11/390,882.
USPTO Office Action dated Apr. 27, 2009 for copending U.S. Appl. No. 11/390,655.
USPTO Office Action dated Apr. 27, 2009 for copending U.S. Appl. No. 11/391,137.
USPTO Office Action dated Mar. 16, 2009 for copending U.S. Appl. No. 11/391,485.
USPTO Office Action dated Apr. 15, 2009 for copending U.S. Appl. No. 12/091,566.
USPTO Notice of Allowance dated Apr. 13, 2009 for copending U.S. Appl. No. 11/391,063.
USPTO Office Action dated Apr. 16, 2009 for copending U.S. Appl. No. 12/091,570.
USPTO Office Action dated Apr. 17, 2009 for copending U.S. Appl. No. 11/390,671.
USPTO Office Action dated Apr. 17, 2009 for copending U.S. Appl. No. 11/391,565.
USPTO Office Action dated Apr. 20, 2009 for copending U.S. Appl. No. 11/390,631.
USPTO Office Action dated Mar. 31, 2009 for copending U.S. Appl. No. 11/390,563.
USPTO Office Action dated Apr. 2, 2009 for copending U.S. Appl. No. 11/390,793.
USPTO Office Action dated Mar. 23, 2009 for copending U.S. Appl. No. 11/390,752.
USPTO Office Action dated Mar. 23, 2009 for copending U.S. Appl. No. 11/390,794.
USPTO Office Action dated May 13, 2009 for copending U.S. Appl. No. 12/361,779.
USPTO Office Action dated May 13, 2009 for copending U.S. Appl. No. 12/365,515.
USPTO Office Action dated May 21, 2009 for copending U.S. Appl. No. 11/706,476.
USPTO Office Action dated May 22, 2009 for copending U.S. Appl. No. 11/706,791.
USPTO Office Action dated May 18, 2009 for copending U.S. Appl. No. 11/391,505.
USPTO Office Action dated Apr. 14, 2009 for copending U.S. Appl. No. 11/635,434.
USPTO Office Action dated Apr. 14, 2009 for copending U.S. Appl. No. 11/635,433.
USPTO Office Action dated May 18, 2009 for copending U.S. Appl. No. 11/390,846.
USPTO Office Action dated Jun. 11, 2009 for copending U.S. Appl. No. 11/390,809.
USPTO Office Action dated Jul. 2, 2009 for copending U.S. Appl. No. 11/390,827.
USPTO Office Action dated Aug. 7, 2009 for copending U.S. Appl. No. 11/390,773.
USPTO Office Action dated Aug. 27, 2009 for copending U.S. Appl. No. 11/390,826.
USPTO Office Action dated Aug. 10, 2009 for copending U.S. Appl. No. 11/390,722.
Dixon, E.R. et al., "The Inter-Relation of Some Mechanical Properties with Molecular Weight and Crystallinity in Poly(ethylene terephthalate)", 1968, pp. 464-470, Journal of Materials Science, vol. 3.
USPTO Office Action dated Sep. 4, 2009, for copending U.S. Appl. No. 11/391,124.
USPTO Office Action dated Sep. 10, 2009, for copending U.S. Appl. No. 11/390,812.
New Copending U.S. Appl. No. 12/479,893, filed Jun. 8, 2009, Emmett Dudley Crawford, et al.
USPTO Office Action dated Sep. 14, 2009 for copending U.S. Appl. No. 11/391,576.
Ellis, Thomas S., "Miscibility of Polyamide Blends: Effects of Configuration," 1995, Polymer, vol. 36, Issue 20, pp. 3919-3926.
Buschow, K.H.J., et al., "Packaging: Papers for Sacks and Bags," 2001, Encyclopedia of Materials: Science and Technology, vol. 8, Elsevier, pp. 6646-6652.
Coles, Richard, et al., "Food Packaging Technology," 2003, pp. 194-195 and 224-229, Blackwell Publishing.
Sajiki, Junko, et al., "Leaching of Bisphenol A (BPA) to Seawater from Polycarbonate Plastic and its Degradation by Reactive Oxygen Species," 2003, Chemosphere, 51, pp. 55-62.
USPTO Office Action dated Oct. 2, 2009 for copending U.S. Appl. No. 11/588,524.
USPTO Office Action dated Oct. 7, 2009 for copending U.S. Appl. No. 11/588,458.
USPTO Office Action dated Sep. 29, 2009 for copending U.S. Appl. No. 11/390,751.
USPTO Office Action dated Sep. 24, 2009 for copending U.S. Appl. No. 11/588,883.
USPTO Office Action dated Sep. 28, 2009 for copending U.S. Appl. No. 11/390,847.
USPTO Office Action dated Sep. 24, 2009 for copending U.S. Appl. No. 11/390,858.
USPTO Office Action dated Sep. 29, 2009 for copending U.S. Appl. No. 11/390,629.
USPTO Office Action dated Sep. 29, 2009 for copending U.S. Appl. No. 11/390,814.
USPTO Office Action dated Oct. 19, 2009 for copending U.S. Appl. No. 11/390,563.
USPTO Office Action dated Oct. 20, 2009 for copending U.S. Appl. No. 11/588,907.
USPTO Office Action dated Oct. 21, 2009 for copending U.S. Appl. No. 11/391,156.
Gupta, V.B. et al., "PET Fibers, Films, and Bottles: Section 5-7", Handbook of Thermoplastic Polyesters: Homopolymers, Copolymers, Blends, and Composites, 2005, pp. 362-388, Wiley InterScience.

USPTO Office Action dated Oct. 22, 2009 for copending U.S. Appl. No. 11/588,906.
USPTO Office Action dated Nov. 3, 2009 for copending U.S. Appl. No. 11/390,883.
USPTO Office Action dated Nov. 4, 2009 for copending U.S. Appl. No. 11/390,750.
USPTO Office Action dated Nov. 4, 2009 for copending U.S. Appl. No. 11/390,864.
USPTO Office Action dated Nov. 17, 2009 for copending U.S. Appl. No. 12/254,894.
USPTO Office Action dated Nov. 18, 2009 for copending U.S. Appl. No. 11/390,630.
USPTO Office Action dated Nov. 30, 2009 for copending U.S. Appl. No. 11/391,495.
Turner, S.R., et al., "Amorphous and Crystalline Polyesters based on 1,4-Cyclohexanedimethanol", Chapter 7, Modern Polyesters: Chemistry and Technology of Polyesters and Copolyesters, Edited by J. Sheirs and T.E. Long, 2003 John Wiley & Sons, Ltd., pp. 267-292.
USPTO Office Action dated Nov. 18, 2009 for copending U.S. Appl. No. 11/390,794.
USPTO Office Action dated Nov. 20, 2009 for copending U.S. Appl. No. 11/391,485.
USPTO Office Action dated Nov. 20, 2009 for copending U.S. Appl. No. 11/390,882.
USPTO Office Action dated Dec. 1, 2009 for copending U.S. Appl. No. 12/091,570.
USPTO Office Action dated Dec. 3, 2009 for copending U.S. Appl. No. 11/395,505.
USPTO Office Action dated Dec. 4, 2009 for copending U.S. Appl. No. 12/091,566.
Zipper, Marcus D.,et al., "A Free Volume Study of Miscible Polyester Blends," 1995, pp. 127-136, Polymer International, vol. 36.
"APEC High-Heat Polycarbonate Resin," 2004, Bayer Material Science Product Information Not Prior Art; Submitted for State of the Art.
Lobo, Hubert et al, "Handbook of Plastics Analysis," 2003, pp. 20 and 21, Marcel Dekker, Inc.
USPTO Notice of Allowance dated Dec. 11, 2009 for copending U.S. Appl. No. 12/365,515.
USPTO Office Action dated Dec. 18, 2009 for copending U.S. Appl. No. 11/390,846.
Copending U.S. Appl. No. 12/639,324, filed on Dec. 16, 2009.
USPTO Notice of Allowance dated Dec. 22, 2009 for copending U.S. Appl. No. 12/361,779.
USPTO Office Action dated Jan. 7, 2010 for copending U.S. Appl. No. 12/091,568.
USPTO Office Action dated Jan. 13, 2010 for copending U.S. Appl. No. 11/635,433.
USPTO Office Action dated Jan. 14, 2010 for copending U.S. Appl. No. 11/390,809.
USPTO Notice of Allowance dated Jan. 27, 2010 for copending U.S. Appl. No. 11/635,434.
USPTO Office Action dated Mar. 11, 2010, for copending U.S. Appl. No. 11/391,124.
Copending Application U.S. Appl. No. 12/724,492, filed on Mar. 16, 2010.
Copending Application U.S. Appl. No. 12/724,480, filed on Mar. 16, 2010.
Copending Application U.S. Appl. No. 12/724,468, filed on Mar. 16, 2010.
USPTO Office Action dated Mar. 19, 2010, for copending U.S. Appl. No. 11/588,527.
USPTO Notice of Allowance dated Mar. 24, 2010 for copending U.S. Appl. No. 11/391,565.
USPTO Office Action dated Mar. 29, 2010 for copending U.S. Appl. No. 11/390,812.
USPTO Notice of Allowance dated Apr. 15, 2010 for copending U.S. Appl. No. 11/391,505.
USPTO Office Action dated Apr. 19, 2010 for copending U.S. Appl. No. 12/724,480.
USPTO Office Action dated Apr. 21, 2010 for copending U.S. Appl. No. 12/724,468.
USPTO Office Action dated Apr. 21, 2010 for copending U.S. Appl. No. 12/724,492.
USPTO Office Action dated May 6, 2010 for copending U.S. Appl. No. 12/254,894.
New copending U.S. Appl. No. 12/784,193, filed on May 20, 2010, Emmett Dudley Crawford, et al.
USPTO Notice of Allowance dated May 13, 2010 for copending U.S. Appl. No. 11/390,629.
USPTO Notice of Allowance dated May 13, 2010 for copending U.S. Appl. No. 11/390,751.
USPTO Notice of Allowance dated May 21, 2010 for copending U.S. Appl. No. 11/391,156.
USPTO Notice of Allowance dated May 26, 2010 for copending U.S. Appl. No. 11/391,495.
USPTO Notice of Allowance dated Jun. 24, 2010 for copending U.S. Appl. No. 11/391,576.
USPTO Office Action dated Jun. 24, 2010 for copending U.S. Appl. No. 11/390,846.
USPTO Office Action dated Jul. 8, 2010 for copending U.S. Appl. No. 11/390,809.
USPTO Notice of Allowance dated Jul. 8, 2010 for copending U.S. Appl. No. 11/390,630.
USPTO Notice of Allowance dated Jul. 8, 2010 for copending U.S. Appl. No. 11/390,883.
USPTO Office Action dated Jul. 12, 2010 for copending U.S. Appl. No. 11/390,794.
Notice of Allowance dated Jul. 13, 2010 for copending U.S. Appl. No. 11/391,505.
USPTO Office Action dated Jul. 22, 2010 for copending U.S. Appl. No. 12/479,893.
USPTO Notice of Allowance dated Jul. 22, 2010 for copending U.S. Appl. No. 11/391,485.
USPTO Notice of Allowance dated Aug. 3, 2010 for copending U.S. Appl. No. 11/390,864.
USPTO Office Action dated Aug. 6, 2010 for copending U.S. Appl. No. 11/773,275.
New copending U.S. Appl. No. 12/853,717, filed on Aug. 10, 2010, Emmett Dudley Crawford, et al.
USPTO Notice of Allowance dated Aug. 11, 2010 for copending U.S. Appl. No. 11/390,631.
USPTO Notice of Allowance dated Sep. 2, 2010 for copending U.S. Appl. No. 11/390,811.
USPTO Office Action dated Sep. 2, 2010 for copending U.S. Appl. No. 11/391,124.
New copending U.S. Appl. No. 12/888,648, filed on Sep. 23, 2010, Thomas Joseph Pecorini et al.
USPTO Office Action dated Oct. 5, 2010 for copending U.S. Appl. No. 11/390,655.
New copending U.S. Appl. No. 12/900,060, filed on Oct. 7, 2010, Thomas Joseph Pecorini, et al.
USPTO Office Action dated Oct. 8, 2010 for copending U.S. Appl. No. 11/390,812.
USPTO Notice of Allowance dated Oct. 28, 2010 for copending U.S. Appl. No. 11/390,827.
USPTO Office Action dated Oct. 27, 2010 for copending U.S. Appl. No. 12/294,690.
New Copending U.S. Appl. No. 12/900,060, filed on Oct. 7, 2010, Joseph Thomas Pecorini.
USPTO Notice of Allowance dated Oct. 14, 2010 for copending U.S. Appl. No. 11/390,722.
USPTO Notice of Allowance dated Nov. 2, 2010 for copending U.S. Appl. No. 12/724,480.
USPTO Notice of Allowance dated Nov. 4, 2010 for copending U.S. Appl. No. 12/724,468.
USPTO Notice of Allowance dated Nov. 4, 2010 for copending U.S. Appl. No. 11/390,955.
USPTO Office Action dated Nov. 4, 2010 for copending U.S. Appl. No. 12/294,686.
USPTO Notice of Allowance dated Nov. 4, 2010 for copending U.S. Appl. No. 11/390,826.
USPTO Office Action dated Oct. 27, 2010 for copending U.S. Appl. No. 11/390,836.

USPTO Notice of Allowance dated Nov. 23, 2010 for copending U.S. Appl. No. 11/390,563.
New copending U.S. Appl. No. 12/943,217, filed on Nov. 10, 2010, Emmett Dudley Crawford et al.
New copending U.S. Appl. No. 12/963,703, filed on Dec. 9, 2010.
New copending U.S. Appl. No. 13/007,838, filed on Jan. 17, 2011, Emmett Dudley Crawford et al.
USPTO Office Action dated Jan. 24, 2011 for copending U.S. Appl. No. 11/773,275.
New copending U.S. Appl. No. 13/016,147, filed on Jan. 28, 2011, Emmett Dudley Crawford, et al.
New copending U.S. Appl. No. 13/017,069, filed on Jan. 31, 2011, Emmett Dudley Crawford, et al.
New Copending U.S. Appl. No. 13/017,352, filed on Jan. 31, 2011, Emmett Dudley Crawford, et al.
USPTO Office Action dated Jan. 25, 2011 for copending U.S. Appl. No. 12/853,717.
Al-Malaika, S., "Stabilization", Encyclopedia of Polymer Science and Technology, vol. 4, 2001, pp. 179-229, John Wiley & Sons, Inc.
USPTO Notice of Allowance dated Jan. 26, 2011 for copending U.S. Appl. No. 11/390,858.
USPTO Office Action dated Feb. 2, 2011 for copending U.S. Appl. No. 11/390,655.
USPTO Office Action dated Mar. 17, 2011 for copending U.S. Appl. No. 12/479,893.
USPTO Notice of Allowance dated Mar. 17, 2011 for copending U.S. Appl. No. 11/391,137.
USPTO Office Action dated Feb. 14, 2011 for copending U.S. Appl. No. 12/294,690.
USPTO Notice of Allowance dated Feb. 18, 2011 for copending U.S. Appl. No. 11/390,809.
USPTO Notice of Allowance dated Feb. 17, 2011 for copending U.S. Appl. No. 11/390,812.
New Copending U.S. Appl. No. 13/097,701, filed on Apr. 29, 2011, Michael Eugene Donelson, et al.
USPTO Office Action dated Jun. 2, 2011 for copending U.S. Appl. No. 12/338,453.
USPTO Office Action dated Jun. 16, 2011 for copending U.S. Appl. No. 12/390,694.
USPTO Notice of Allowance dated Aug. 12, 2011 for copending U.S. Appl. No. 11/390,752.
USPTO Office Action dated Jul. 19, 2011 for copending U.S. Appl. No. 11/390,794.
USPTO Notice of Allowance dated Jul. 21, 2011 for copending U.S. Appl. No. 11/390,671.
USPTO Notice of Allowance dated Aug. 3, 2011 for copending U.S. Appl. No. 11/390,655.
New copending U.S. Appl. No. 13/162,870, filed on Jun. 17, 2011, Emmett Dudley Crawford, et al.
USPTO Office Action dated Jul. 7, 2011 for copending U.S. Appl. No. 11/588,906.
USPTO Office Action dated Jun. 22, 2011 for copending U.S. Appl. No. 12/091,570.
USPTO Office Action dated Jun. 8, 2011 for copending U.S. Appl. No. 11/588,883.
USPTO Office Action dated Aug. 17, 2011 for copending U.S. Appl. No. 12/274,692.
New copending U.S. Appl. No. 13/215,511, filed on Aug. 23, 2011, Emmett Dudley Crawford, et al.
USPTO Office Action dated Sep. 14, 2011 for copending U.S. Appl. No. 13/017,069.
USPTO Notice of Allowance dated Sep. 16, 2011 for copending U.S. Appl. No. 11/390,671.
USPTO Notice of Allowance dated Sep. 16, 2011 for copending U.S. Appl. No. 12/784,193.
USPTO Office Action dated Oct. 17, 2011 for copending U.S. Appl. No. 12/853,717.
USPTO Notice of Allowance dated Oct. 17, 2011 for copending U.S. Appl. No. 11/390,794.
USPTO Notice of Allowance dated Oct. 25, 2011 for copending U.S. Appl. No. 12/900,060.
USPTO Office Action dated Oct. 31, 2011 for copending U.S. Appl. No. 12/639,324.
USPTO Office Action dated Nov. 2, 2011 for copending U.S. Appl. No. 12/479,893.
USPTO Notice of Allowance dated Nov. 2, 2011 for copending U.S. Appl. No. 12/390,694.
USPTO Notice of Allowance dated Nov. 10, 2011 for copending U.S. Appl. No. 12/943,217.
USPTO Notice of Allowance dated Nov. 28, 2011 for copending U.S. Appl. No. 12/274,692.
New copending U.S. Appl. No. 13/330,052, filed Dec. 19, 2011, Kenny Randolph Parker, et al.
USPTO Notice of Allowance dated Dec. 20, 2011 for copending U.S. Appl. No. 12/390,694.
USPTO Office Action dated Dec. 21, 2011 for copending U.S. Appl. No. 12/091,570.
New copending U.S. Appl. No. 13/348,677, filed on Jan. 12, 2012, Emmett Dudley Crawford, et al.
USPTO Notice of Allowance dated Feb. 14, 2012 for copending U.S. Appl. No. 11/588,906.
New copending U.S. Appl. No. 13/398,262, filed on Feb. 26, 2012, Emmett Dudley Crawford, et al.
Hasek, et al. Chemistry of Dimethylketone Dimer. Journal of Organic Chemistry, 1961, vol. 26, pp. 700-704.
Sprague et al., Hydrogentation and Hydrogenolysis of 1,3-Diketones. Journal of the American Chemical Society, 1934, vol. 56, pp. 2669-2675.
Coover, H. et al., "Copolyester Molding Compositions," Chemical Abstracts Service, XP002391844, 1970.
Bergen, R. L., Jr., "Stress Cracking of Rigid Thermoplastics," SPE Journal, pp. 667-669, Jun. 1962.
2866-43-5. Registry [>database>online].  Chemical Abstracts Services, a division of the American Chemical Society [retrieved on Nov. 6, 2006]. Retrieved from: SciFinder.
7128-64-5. Registry [>database>online]. Chemical Abstracts Services, a division of the American Chemical Society [retrieved on Nov. 6, 2006]. Retrieved from: SciFinder.
USPTO Office Action mailed Aug. 29, 2012 for copending U.S. Appl. No. 12/963,703.
USPTO Notice of Allowance mailed Nov. 5, 2012 for copending U.S. Appl. 12/963,703.
USPTO Office Action mailed Aug. 30, 2012 for copending U.S. Appl. No. 12/963,691.
International Search report and Written Opinion of the International Searching Authority mailed Feb. 14, 2012 for International Application No. PCT/US2011/062782.
Nternational Search report and Written Opinion of the International Searching Authority mailed Jan. 16, 2012 for International Application No. PCT/US2011/062178.

Hydrogenation of 2,2,4,4-Tetraalkycyclobutane-1,3-dione
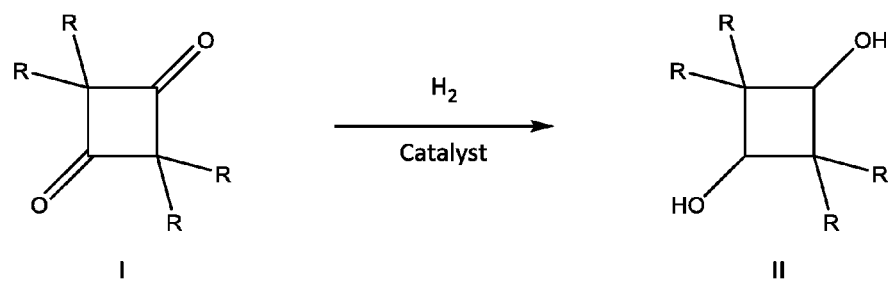

PROCESS FOR THE PREPARATION OF 2,2,4,4-TETRAALKYLCYCLOBUTANE-1,3-DIOLS

FIELD OF THE INVENTION

This invention pertains to a process for the preparation of a diol from the corresponding dione. In particular, this invention pertains a process for the preparation of a 2,2,4,4-tetraalkylcyclobutane-1,3-diol by hydrogenation of a 2,2,4,4-tetraalkylcyclobutane-1,3-dione in the vapor phase in the presence of a supported catalyst.

BACKGROUND OF THE INVENTION

Tetraalkylcyclobutane-1,3-diols can be important intermediates for producing a variety of polymeric materials which possess advantageous properties. For example, polyesters derived from dicarboxylic acids and 2,2,4,4-tetramethylcyclobutane-1,3-diol possess higher glass transition temperatures, superior weatherability, and hydrolytic stability compared to polyesters prepared from other commonly-used diols. Tetraalkylcyclobutane-1,3-diols can be prepared by the catalytic hydrogenation of the corresponding 2,2,4,4-tetraalkylcyclobutane-1,3-dione (I) to the corresponding 2,2,4,4-tetraalkylcyclobutane-1,3-diol (II), wherein R is an alkyl group, as illustrated in FIG. 1.

The hydrogenation of the corresponding tetraalkylcyclobutanediones can be carried out using a variety of catalysts such as, for example, nickel, ruthenium, and cobalt. For example, the hydrogenation of 2,2,4,4-tetramethylcyclobutane-1,3-dione to 2,2,4,4-tetramethylcyclobutane-1,3-diol can be accomplished using nickel or ruthenium containing catalysts as described in U.S. Pat. Nos. 3,000,906, 3,190,928; 5,169,994; 5,258,556; and 2,936,324. Cobalt containing catalysts also can be used. For example, U.S. Pat. Nos. 5,528,556 and 5,169,994 disclose that Raney cobalt is effective for hydrogenation of 2,2,4,4-tetramethylcyclobutane-1,3-dione to 2,2,4,4-tetramethylcyclobutane-1,3-diol. These processes, however, can exhibit long reaction times. The reaction rate can be increased by raising the temperature and pressure, but these measures can be expensive and can result in the formation of by-products from the decomposition of the products and starting materials.

In general, the hydrogenation of 2,2,4,4-tetramethylcyclobutane-1,3-dione produces the corresponding 2,2,4,4-tetramethylcyclobutane-1,3-diol as a mixture of cis and trans isomers. For example, U.S. Pat. No. 3,190,928 discloses a process for hydrogenation of 2,2,4,4-tetramethylcyclobutane-1,3-dione to 2,2,4,4-tetramethylcyclobutane-1,3-diol using nickel- or ruthenium-based catalysts that produce cis:trans molar ratios ranging from about 0.5:1 to about 1.2:1 depending on reaction conditions. A wide variation in the cis:trans ratio, however, can result in polyesters with inconsistent and/or undesirable properties. In addition, for some applications, a high cis:trans ratio is desirable, but catalysts that produce a high ratio of cis:trans isomers may not give the good yields or acceptable rates of hydrogenation.

There is a need in the art, therefore, for a process that can produce 2,2,4,4-tetramethylcyclobutanediol at good conversions and selectivities and with consistently high cis:trans isomer ratios, e.g., greater than 1:1. There is also a need for such a process that can be operated economically at modest pressures and temperatures.

SUMMARY OF THE INVENTION

We have discovered that 2,2,4,4-tetraalkylcyclobutane-1,3-diols having high cis:trans ratios can be prepared efficiently by vapor-phase hydrogenation the corresponding 2,2,4,4-tetraalkylcyclobutane-1,3-dione in the presence of nickel or ruthenium catalysts. A general embodiment of our invention, therefore, is a process for the preparation of a 2,2,4,4-tetraalkylcyclobutane-1,3-diol, comprising:

I. continuously feeding to a hydrogenation zone hydrogen and a hydrogenatable reactant comprising a 2,2,4,4-tetraalkylcyclobutane-1,3-dione having the formula (I):

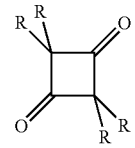

wherein the hydrogen and hydrogenatable reactant are in the gas phase and R is a alkyl radical containing 1 to 8 carbon atoms;

II. continuously contacting the hydrogen and hydrogenatable reactant of step (I) under hydrogenation conditions of temperature and pressure with a catalyst comprising nickel, ruthenium, or combination thereof, to form a hydrogenation product comprising a 2,2,4,4-tetraalkylcyclobutane-1,3-diol having the formula

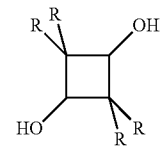

wherein the temperature is greater than the dew point of the hydrogenation product; and III. continuously recovering from the reaction zone a gaseous effluent comprising the hydrogenation product.

In general, our process can produce 2,2,4,4-tetraalkylcyclobutane-1,3-diols in high yields an can be operated with increased safety and operating economy at modest pressures and temperatures.

Our process may be used, in particular, for the preparation of 2,2,4,4-tetramethylcyclobutane-1,3-diol from 2,2,4,4-tetramethylcyclobutane-1,3-dione, and can be carried out under modest pressures and temperatures under continuous operating conditions. The process can give 2,2,4,4-tetramethylcyclobutane-1,3-diol product with an excess of the cis isomer. Thus, another aspect of the invention is a process for the preparation of 2,2,4,4-tetramethylcyclobutane-1,3-diol, comprising I. continuously feeding to a hydrogenation zone hydrogen and a hydrogenatable reactant comprising 2,2,4,4-tetramethylcyclobutane-1,3-dione wherein the hydrogen and hydrogenatable reactant are in the gas phase;

II. continuously contacting the hydrogen and hydrogenatable reactant of step (I) at a temperature of about 100 to about 200° C. and a pressure of about 7 to about 28 bar with a catalyst comprising about 1 to about 8 weight percent ruthenium, based on the total weight of the catalyst, deposited on a support, to form a hydrogenation product comprising 2,2,4,4-tetramethylcyclobutane-1,3-diol having a cis:trans ratio of about 1:1 to about 1.6:1, wherein the temperature is greater than the dew point of the hydrogenation product;

III. continuously recovering from the reaction zone a gaseous effluent comprising the hydrogenation product; and
IV. continuously recycling a portion of the gaseous effluent to the hydrogenation zone.

We have found that ruthenium deposited on activated carbon, carbonized polysulfonated vinylaromatic polymer particles, graphitized carbon, or combinations thereof, are useful catalysts for our novel process. Therefore, another embodiment of our invention is a process for the preparation of 2,2,4,4-tetramethylcyclobutane-1,3-diol, comprising:
I. continuously feeding to a hydrogenation zone hydrogen and a hydrogenatable reactant comprising 2,2,4,4-tetramethylcyclobutane-1,3-dione at a hydrogen: 2,2,4,4-tetramethylcyclobutane-1,3-dione molar ratio of about 100:1 to about 500:1, wherein the hydrogen and hydrogenatable reactant are in the gas phase;
II. continuously contacting the hydrogen and hydrogenatable reactant of step (I) at a temperature of about 100 to about 160° C. and a pressure of about 14 to about 21 bars with a catalyst comprising about 1 to about 8 weight percent ruthenium, based on the total weight of the catalyst, deposited on a support comprising activated carbon, carbonized polysulfonated vinylaromatic polymer particles, carbonized phenol formaldehyde resin particles, graphitized carbon, or combinations thereof, to form a hydrogenation product comprising 2,2,4,4-tetramethylcyclobutane-1,3-diol having a cis:trans ratio of about 1:1 to about 1.6:1, wherein the temperature is greater than the dew point of the hydrogenation product;
III. continuously recovering from the reaction zone a gaseous effluent comprising the hydrogenation product.

The vapor-phase hydrogenation process may be carried in the presence or absence of a solvent and in a variety of reactor types such as, tubular fixed bed, moving bed, or fluidized bed.

DESCRIPTION OF DRAWING

FIG. 1 represents the catalytic hydrogenation of 2,2,4,4-tetraalkylcyclobutane-1,3-dione into the corresponding 2,2,4,4-tetraalkylcyclobutane-1,3-diol.

DETAILED DESCRIPTION

The invention provides a process for the preparation of 2,2,4,4-tetraalkylcyclobutane-1,3-diols such as, for example, 2,2,4,4-tetramethylcyclobutane-1,3-diol, by hydrogenation of the corresponding 2,2,4,4-tetraalkylcyclobutane-1,3-dione in the vapor-phase in presence of ruthenium or nickel catalysts. A general embodiment of our invention, therefore, is a process for the preparation of a 2,2,4,4-tetraalkylcyclobutane-1,3-diol, comprising:
I. continuously feeding to a hydrogenation zone hydrogen and a hydrogenatable reactant comprising a 2,2,4,4-tetraalkylcyclobutane-1,3-dione having the formula

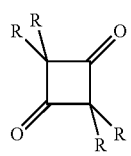

I wherein the hydrogen and hydrogenatable reactant are in the gas phase and R is a alkyl radical containing 1 to 8 carbon atoms;

II. continuously contacting the hydrogen and hydrogenatable reactant of step (I) under hydrogenation conditions of temperature and pressure with a catalyst comprising nickel, ruthenium, or combination thereof, to form a hydrogenation product comprising a 2,2,4,4-tetraalkylcyclobutane-1,3-diol having the formula (II):

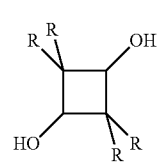

II wherein the temperature is greater than the dew point of the hydrogenation product; and
III. continuously recovering from the reaction zone a gaseous effluent comprising the hydrogenation product.

Unless otherwise indicated, all numbers expressing quantities of ingredients, properties such as molecular weight, reaction conditions, and so forth used in the specification and claims are to be understood as being modified in all instances by the term "about." Unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "C1 to C5 hydrocarbons", is intended to specifically include and disclose C1 and C5 hydrocarbons as well as C2, C3, and C4 hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

Also, it is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

The term "hydrogenatable reactant," as used herein, is intended to mean a substance that is introduced into a hydrogenation reactor that is capable of undergoing a hydrogenation reaction, that is the addition of hydrogen across a double or triple bond between two chemical elements, typically, a carbon-carbon double bond or carbon-oxygen double bond, in the presence of a catalyst. As used herein, the terms "tetraalkylcyclobutanediol," "tetraalkylcyclobutanedione," "tetramethylcyclobutanedione," and "tetramethylcyclobutanediol" are understood to be synonymous with the terms "2,2, 4,4-tetraalkylcyclobutane-1,3-diol," "2,2,4,4-tetraalkylcyclobutane-1,3-dione," and "2,2,4,4-tetramethylcyclobutane-1,3-diol," respectively. The terms "ruthenium" and "nickel" are understood to encompass all the various forms of the metals including elemental ruthenium and nickel as well as any compounds of ruthenium and nickel such as, for example, those containing oxygen, halide, trivalent nitrogen, carbon monoxide, hydrogen, carboxylates, and diones, either alone or in any combination.

Our invention provides a process for the preparation of a 2,2,4,4-tetraalkylcyclobutane-1,3-diol having the formula (II) by continuously feeding to a hydrogenation zone hydrogen and a hydrogenatable reactant comprising a 2,2,4,4-tetraalkylcyclobutane-1,3-dione having the formula (I) as shown in FIG. 1, wherein the R groups are identical, alkyl radicals having 1 to 8 carbon atoms. For example, the alkyl radicals represented by R can comprise 1 to 6 carbon atoms, 1 to 4 carbon atoms, or 1 to 2 carbon atoms. The alkyl radicals may be linear, branched or a combination of linear and branched alkyl radicals. Representative alkyl groups include, but are not limited to, methyl, ethyl, propyl, isopropyl, butyl, isobutyl, pentyl, isoamyl, hexyl, heptyl, and octyl. Some examples of 2,2,4,4-tetralkylcyclobutane-1,3-diones that can be hydrogenated in the process of the invention include 2,2,4,4-tetramethylcyclobutane-1,3-dione, 2,2,4,4-tetraethylcyclobutane-1,3-dione, 2,2,4,4-tetra-n-propylcyclobutane-1,3-dione, 2,2,4,4-tetraisopropylcyclobutane-1,3-dione, 2,2,4,4-tetra-n-butylcyclobutane-1,3-dione, 2,2,4,4-tetraisobutylcyclobutane-1,3-dione, 2,2,4,4-tetra-n-amylcyclobutane-1,3-dione, 2,2,4,4-tetraisoamylcyclobutane-1,3-dione, 2,2,4,4-tetra-n-hexylcyclobutane-1,3-dione, 2,2,4,4-tetra-n-heptylcyclobutane-1,3-dione, and 2,2,4,4-tetra-n-octylcyclobutane-1,3-dione. In one embodiment of the invention, for example, the hydrogenatable reactant comprises 2,2,4,4-tetramethylcyclobutane-1,3-dione (R is methyl in Formula I) and produces a hydrogenation product comprising 2,2,4,4-tetramethylcyclobutane-1,3-diol (R is methyl in Formula II).

The hydrogenation process comprises continuously feeding to a hydrogenation zone hydrogen and a hydrogenatable reactant comprising a 2,2,4,4-tetraalkylcyclobutane-1,3-dione. The source and purity of the hydrogen gas used in the processes of the present invention are not critical. The hydrogen gas may comprise fresh hydrogen or a mixture of fresh hydrogen and recycle hydrogen. The hydrogen gas can be a mixture of hydrogen, optionally minor amounts, typically less than about 30 mole %, of components such as CO and $CO_2$, and inert gases, such as argon, nitrogen, or methane. Typically, the hydrogen gas can comprise at least 70 mole % of hydrogen. For example, the hydrogen gas can comprise at least 90 mole % or, in another example, at least 97 mole %, of hydrogen. The hydrogen gas can be obtained from any of the conventional sources well known in the art such as, for example, by partial oxidation or steam reforming of natural gas. Pressure swing absorption can be used if a high purity hydrogen gas is desired. If hydrogen gas recycle is utilized in the process, then the recycled hydrogen gas will normally contain minor amounts of one or more products of the hydrogenation reaction, i.e., 2,2,4,4-tetraalkylcyclobutane-1,3-diols, which have not been fully condensed in the product recovery stage downstream from the hydrogenation zone.

The hydrogenatable reactant and hydrogen can be contacted continuously under hydrogenation conditions of temperature and pressure with any catalyst capable of catalysing the hydrogenation of a ketone or carbonyl group to the corresponding alcohol or mixture of alcohols. Typical catalysts can include copper-containing catalysts and Group VIII metal-containing catalysts. For example, the catalyst can comprise copper chromite, nickel, ruthenium, palladium, platinum, cobalt, iridium, or combinations thereof. The term "copper chromite", as used herein, is intended have its commonly understood meaning in the art and includes copper chromite itself as represented by the general formula, $CuCr_2Ox$, non-stoichiometric mixed copper-chromium oxides, prepared by coprecipitation, and the various mixtures of copper chromite with copper metal, copper oxides, and chromium oxides that may be formed during the catalyst manufacturing process and its subsequent use as a hydrogenation catalyst. For example, the copper chromite, as prepared, may comprise one or more of: copper (II) oxide, copper chromite ($CuCr_2O_4$), chromium trioxide ($CrO_3$), or chromic oxide ($Cr_2O_3$). In one embodiment of the invention, for example, the copper chromite may comprise about 24-26 weight % copper(II) oxide, about 65-67 weight % copper chromite, about 1 weight % chromium trioxide, about 1 weight % chromic oxide, and about 0-4 weight % graphite. During the hydrogenation process, a portion of the copper oxide may be reduced to copper metal. Thus, under hydrogenation conditions, the copper chromite of the invention can comprise mixtures of copper chromite, copper oxides, chromium oxides, and copper metal in various proportions. The copper chromite component of the catalysts can be prepared using conventional coprecipitation techniques well known in the art. In addition, the copper chromite may be further compounded with binders to aid in pellet formation or supported on additional support materials such as, for example, alumina, titania, carbon, graphite, zirconia, silica, silica-alumina, and the like.

Some additional examples of suitable copper-containing catalysts include reduced copper-on-alumina catalysts, reduced copper oxide/zinc oxide catalysts, with or without a promoter, and reduced manganese promoted copper catalysts. Suitable copper oxide/zinc oxide catalyst precursors include CuO/ZnO mixtures wherein the Cu:Zn weight ratio ranges from about 0.4:1 to about 2:1. Promoted copper oxide/zinc oxide precursors include CuO/ZnO mixtures wherein the Cu:Zn weight ratio ranges from about 0.4:1 to about 2:1 and which are promoted with about 0.1% by weight to about 15% by weight of barium, manganese or a mixture of barium and manganese. For example, manganese promoted copper catalyst precursors typically have a Cu:Mn weight ratio of from about 2:1 to about 10:1 and can include an alumina support, in which case the Cu:Al weight ratio typically can be from about 2:1 to about 4:1. Many of these catalysts are available commercially from Davy Research and Development Limited or BASF Catalysts.

The catalyst may comprise Group VIII metal catalysts such as, for example, cobalt, platinum, ruthenium, nickel, rhodium, iridium, and palladium catalysts. For example, various cobalt catalysts, such as metallic, alloy, and supported cobalt, may be used. An example of metallic and alloy cobalt is Raney® cobalt from W.R. Grace Co. The cobalt also may be deposited on the various support materials described herein. In one embodiment, or example, the catalyst can comprise metallic nickel or metallic ruthenium, i.e., as ruthenium or nickel powder, or in the form of a supported catalyst in which the ruthenium or nickel is deposited on a support material. The term "support," as used in the context of the present specification and claims is intended to have its commonly accepted meaning as would be well-understood by persons of ordinary skill in the art, that is, a nominally inert material on which a catalytically active material, e.g., typically a metal, is deposited on. The term, "deposited on," as used herein, is understood to mean any known method for adding the metal to the support including, but not limited to, depositing, adsorption, impregnation, ion-exchange, admixing, comprecipitation, and the like.

When deposited on a support, the amount of the ruthenium contained in the catalyst may range from about 0.01 to about 10 weight percent (abbreviated herein as "wt %") based upon the total weight of the catalyst. For example, the processes of the present invention may use a catalyst comprising about 0.01 to about 10 wt % ruthenium, based on the total weight of the catalyst. Other examples of ruthenium levels on the catalyst are 0.05 to about 7 wt % ruthenium and about 1 to about 5 wt % ruthenium. When, ruthenium metal is used as the catalyst in the absence of support, the weight percent of ruthenium in the catalyst is typically at least 95 to 100 weight percent, based on the total weight of the catalyst.

Similarly, the amount of the nickel compound that may be employed as the catalyst in our process may range from about 0.01 to about 100 weight percent based upon the total weight of the catalyst. For example, the processes of the present invention may use a catalyst comprising about 0.01 to about 80 wt % nickel, based on the total weight of the catalyst. Other examples of nickel levels on the catalyst are 0.05 to about 70 wt % nickel and about 1 to about 50 wt % nickel. For example, in one embodiment, the catalyst can comprise a Raney nickel.

The catalytic metals may be deposited on any recognized support material. For example, the support may comprise materials such as chromia, rare earth metal oxides, mixed metal oxides, zinc oxide, alumina, silica, silica-alumina, silicon carbide, zirconia, titania, carbon, graphite, graphitized carbon, carbon nanotubes, zeolites, carbonized polysulfonated vinylaromatic polymer particles, carbonized phenol-formaldehyde resin spheres, or combinations thereof. These support materials are well-known to persons skilled in the art and many are available commercially. For example, graphitized carbon supports are described in Rossetti et al. *Catalysis Today,* 2005, 102-103, pp. 219-224, and in U.S. Pat. No. 7,115,239. The catalyst support may be further compounded with one or more binders to aid in pellet formation. The catalyst support along with any binder can be fabricated in any of the commonly used forms well-known in the art such as, for example, powders, extrudates, chips, granules, monoliths, pellets, cylinders, rings, saddles, spheres, stars, single lobe or multiple-lobe shapes, and the like. Depending on the particular support material employed and/or the method used to prepare a catalyst, ruthenium may be deposited primarily on the surface of the support or distributed throughout the support.

In one embodiment, the ruthenium and nickel may be deposited on a support comprising carbonized, phenol-formaldehyde resin particles or polysulfonated vinylaromatic polymer particles. As used herein, the term "carbonized, polysulfonated vinylaromatic polymer particles" is understood to mean macroporous copolymers and include macroporous or macroreticular copolymers that have been polysulfonated and then substantially transformed to carbon or a carbonaceous material by pyrolysis or the action of heat. The preparation of the carbonized polysulfonated vinylaromatic polymer particles is described in general in U.S. Pat. No. 4,839,331. Similarly, the term "carbonized phenol-formaldehyde resin particles," is understood to mean polymers prepared by reacting a phenol with an aldehyde in the presence of an acid or a base and transformed into a carbonaceous material by the action of heat. These particles are typically obtained in the form of spheres or beads. The preparation of carbonized phenol-resin particles (beads) is described, for example, in U.S. Patent Application Publication No.'s 20070191571 and 20070191572.

In another embodiment, the catalyst comprises ruthenium or nickel supported on carbon nanotubes. Carbon nanotubes (also known as fibrils) are well-known in the art as vermicular carbon deposits having diameters less than 1.0 µm, preferably less than 0.5 µm, and even more preferably less than 0.2 µm. Carbon nanotubes can be either multi walled (i.e., have more than one graphene layer more or less parallel to the nanotube axis) or single walled (i.e., have only a single graphene layer parallel to the nanotube axis). Other types of carbon nanotubes are also known, such as fishbone fibrils (e.g., wherein the graphene sheets are disposed in a herringbone pattern with respect to the nanotube axis), etc. As produced, carbon nanotubes may be in the form of discrete nanotubes, aggregates of nanotubes (i.e., dense, microscopic particulate structure comprising entangled carbon nanotubes), or a mixture of both. Some representative examples of carbon nanotubes are described in U.S. Patent Application Publication No.'s 2009 0208391; 2008 0176069; 2008 0175787; 2006 0239893; 2006 0142149; 2006 0142148; and 2003 0039604.

It will be apparent to persons skilled in the art that any of the weight percentages of ruthenium or nickel described above can be used on any of the aforementioned supports. For example, the catalyst can comprise about 0.01 to about 10 weight percent ruthenium or about 0.01 to about 80 weight percent nickel, based on the total weight of the catalyst, deposited on a support comprising silica-alumina, titania, alumina-clay, clay, graphite, silicon carbide, zirconium, activated carbon, carbonized phenol formaldehyde resin particles, carbonized polysulfonated vinylaromatic polymer particles, carbon nanotubes, or combinations thereof.

The catalyst may be prepared by conventional techniques such as, for example, vapor deposition or impregnation of a ruthenium or nickel compound into the support material. Nickel or ruthenium may be provided as the metal itself or in the form of well-known ruthenium or nickel compounds such as, for example, salts of inorganic or organic acids, oxides, and organometallic complexes. The support material may be impregnated with ruthenium or nickel metal by immersing the support material in a solution of ruthenium or nickel compound in a suitable solvent or by spraying the support material with the solution. The support material typically is dried and the catalyst exposed to a reducing environment, e.g., hydrogen, in order to reduce the ruthenium or nickel compounds to the corresponding zero-valent metals.

The hydrogenation conditions of pressure and temperature may be varied depending on the activity of the catalyst, the mode of operation, selectivity considerations, and the desired rate of conversion. Our hydrogenation process typically is conducted at temperatures in the range of about 75° C. to about 250° C. Other suitable temperature ranges include about 100 to about 200° C., about 100 to about 180° C., and about 120 to about 160° C. The process can be conducted at pressures in the range of about 689 kPa (100 psi, 7 bar) to about 4134 kPa (600 psi, 42 bar). Further examples of temperatures and pressures at which the process of the invention may be operated are about 120° C. to about 200° C. at a pressure of about 689 kPa (100 psi, 7 bar) to about 2756 kPa (400 psi, 28 bar) and about 130° C. to about 140° C. at a pressure ranging of about 1378 kPa (200 psi, 14 bar) to about 2067 kPa (300 psi, 21 bar).

The temperature and pressure of the reaction are chosen such that the hydrogenatable reactants enter and the products and unconverted reactants leave the hydrogenation zone in the vapor phase. Throughout the present invention, the terms "vapor phase", "gaseous", "vapor state", "vaporous", "gaseous state", and "gas phase" are used interchangeably and are intended to be synonymous. The process of the invention is operated at temperatures above the dew point of the hydrogenation feed and product mixtures. Because the dew point is a complex function of dilution (particularly with respect to non-condensable gases such as hydrogen or inert diluent gases), product composition, and pressure, the process may be operated over a wide range of temperatures, provided the temperature exceeds the dew point of the hydrogenation feed mixtures and product effluent. The term "dew point", as used herein, means the temperature, at a given pressure, at which a gas is saturated with respect to its condensable components and at which condensation occurs. The dew point of the hydrogenation reactants and products of the present invention may be calculated by methods well known to those skilled in the art, for example, as described in Perry's Chemical Engineer's Handbook, 6th ed, (McGraw-Hill), pp. 13-25 through 13-126. Dew points for single product or complex mixtures may be calculated using commercially available engineering computer programs, such as Aspen®, also well-known to those skilled in the art. In practice, as described previously, the process typically operates at a temperature range of about 75 to about 250° C. Other examples of temperature ranges in which our process may operate include about 100 to about 200° C., about 120 to about 200° C., about 100 to about 180° C., about 120 to about 160° C., and about 130 to about 140° C.

A convenient method of forming a gas phase mixture for use in a vapor phase process is to spray liquid 2,2,4,4-tetraalkylcyclobutane-1,3-dione or a 2,2,4,4-tetraalkylcyclobutane-1,3-dione solution into a stream of hot, hydrogen-containing gas to form a saturated or partially saturated vaporous mixture. Alternatively, a vapor mixture can be obtained by bubbling a hot hydrogen-containing gas through the liquid 2,2,4,4-tetraalkylcyclobutane-1,3-dione or 2,2,4,4-tetraalkylcyclobutane-1,3-dione solution. If a saturated vapor mixture is formed it can then be heated further or diluted with more hot gas to produce a partially saturated gaseous mixture prior to contact with the catalyst. To maintain the gaseous feed stream above its dew point at the inlet end of a catalyst bed at the operating pressure, the molar ratio of hydrogen and hydrogenatable reactant fed to the hydrogenation zone may be fed to the hydrogenation zone at a ratio of about 10:1 to about 8000:1. Other molar ratios of hydrogen:hydrogenatable reactant include about 100:1 to about 1000:1, about 100:1 to about 800:1, about 100:1 to about 700:1, and about 100:1 to about 600:1. Typically the feed temperature of the vaporous feed mixture to the hydrogenation zone is at least about 5° C. to about 10° C. above its dew point at the operating pressure.

Although the process of the invention is operated with the feed stream in the gas phase, it is convenient to express the feed rate of the 2,2,4,4-tetraalkylcyclobutane-1,3-dione to the hydrogenation zone as a liquid-hourly space velocity through the hydrogenation catalyst. The liquid-hourly space velocity is expressed as the ratio of the liquid feed rate of the hydrogenatable reactant to the hydrogenation zone to the volume of the hydrogenation catalyst. For example, the process can be operated at a liquid-hourly space velocity of the hydrogenatable reactant through the hydrogenation catalyst can range from about 0.05 to about 4.0 $h^{-1}$. Thus, the hydrogenatable reactant can be fed to the hydrogenation zone at a rate which is equivalent to, per unit volume of catalyst, of about 0.05 to about 4.0 unit volumes of hydrogenarable material per hour (i.e. about 0.05 to about 4.0 $m^3 \, h^{-1}$ per $m^3$ of catalyst). Other examples feed rates expressed as liquid-hourly space velocities are from about 0.1 $h^{-1}$ to about 2.0 $h^{-1}$ and about 0.1 to about 2.0 $h^{-1}$. In one embodiment of the invention, for example, the process is operated at a temperature of about 100 to about 180° C., a pressure of about 7 to about 28 bars absolute, and a liquid-hourly space velocity of about 0.05 to about 4 $hr^{-1}$. Persons of skill in the art will recognize that other combinations of the temperatures, pressures, and feed rates described hereinabove are possible.

Our process forms a hydrogenation product comprising a 2,2,4,4-tetraalkylcyclobutane-1,3-diol. The 2,2,4,4-tetraalkylcyclobutane-1,3-diol hydrogenation product can have a range of cis to trans isomers 0:1 to about 2:1. Other examples of cis:trans ratios are about 0.7:1 to about 1.8:1, about 0.7:1 to about 1.7:1, about 0.7:1 to about 1.6:1, about 0.7:1 to about 1.5:1, about 0.7:1 to about 1.4:1, about 0.7:1 to about 1.3:1, about 0.7:1 to about 1.2:1, about 0.7:1 to about 1.1:1, about 0.7:1 to about 1.0:1, about 0.7:1 to about 0.9:1, and about 0.7:1 to about 0.8:1. For example, in one embodiment of the invention, hydrogenatable reactant can comprise 2,2,4,4-tetramethylcyclobutane-1,3-dione and the hydrogenation product comprises 2,2,4,4-tetramethylcyclobutane-1,3-diol having a cis:trans isomer ratio of about 0.7:1 to about 1.7:1. Some other representative examples of ranges of cis:trans ratios of the product 2,2,4,4-tetramethylcyclobutane-1,3-diol are about 0.7:1 to about 1.6:1, about 0.7:1 to about 1.4:1, about 0.7:1 to about 1.2:1, about 0.7:1 to about 1.0:1, and about 0.7:1 to about 0.8:1.

The hydrogenatable reactant may further comprise a solvent. The solvent may be selected from a wide variety of compounds or mixture of compounds provided that they do not affect adversely the hydrogenation process and are substantially inert or show limited reactivity (e.g., typically less than 1% conversion under process conditions) with respect to the catalyst, hydrogen, the tetraalkylcyclobutanedione starting material, and tetraalkylcyclobutanediol product. The starting 2,2,4,4-tetraalkylcyclobutane-1,3-dione, for example, can be dissolved or partially dissolved in a solvent selected from water, alcohols, ethers, glycols, glycol ethers, alkanes, esters, and mixtures thereof. Some specific examples of solvents that may used in the isomerization process include, but are not limited to, water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, 2,2,4,4-tetramethylcyclobutane-1,3-diol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof. In one embodiment, for example, the solvent comprises isobutyl isobutyrate. In another example, the solvent comprises tetrahydrofuran. Typically, the 2,2,4,4-tetraalkylcyclobutane-1,3-dione can be dissolved in the solvent at a concentration of about 1 to about 60 weight percent, based on the total weight of the tetraalkylcyclobutanedione solution. Some other examples of tetraalkylcyclobutanedione concentrations are about 5 to about 50 weight percent, about 3 to about 25 weight percent, and about 10 to about 25 weight percent. In another example, the tetraalkylcyclobutanedione comprises 2,2,4,4-tetraalkylcyclobutanedione and is dissolved in a solvent comprising isobutyl isobutyrate or tetrahydrofuran at a concentration of about 1 to about 60 weight percent, about 5 to about 50 weight percent, about 3 to about 25 weight percent, or about 10 to about 25 weight percent. Also, it can be economically advantageous to conduct the hydrogenation in the absence of solvent and use the neat, molten 2,2,4,4-tetraalkylcyclobutane-1,3-dione alone or as a mixture with the 2,2,4,4-tetraalkylcyclobutane-1,3-diol as the feed to the process.

For economic and operability reasons, the process can be operated as a continuous process. Continuous operation may utilize a tubular fixed bed with a larger particle size of catalyst such as, for example, granules, pellets, various multilobal shaped pellets, rings, and saddles, or a fluidized bed reactor with smaller particle sizes that can be readily suspended on a column of moving gas. These reactor types are well known to persons skilled in the art. As an example of a continuous process, the catalyst bed may be fixed in a high pressure, tubular or columnar reactor, the vaporous tetraalkylcyclobutanedione fed continuously into the top of the bed at elevated pressure and temperature, and the crude hydrogenation product effluent continuously removed from the base of the reactor. Alternatively, it is possible to feed the tetraalkylcyclobutanedione into the bottom of the bed and continously remove the hydrogenated product effluent from the top of the reactor. It is also possible to use 2 or more catalyst beds connected in parallel or in series to improve conversion, to reduce the quantity of catalyst, or to by pass a catalyst bed for periodic maintenance or catalyst removal. For example, the process may be carried in a similar manner, for example, as in the hydrogenation process disclosed in U.S. Pat. No. 5,395,987.

Our process comprises continuously recovering a gaseous effluent comprising the hydrogenation product. The gaseous effluent, for example, can be recovered using methods well-known to persons skilled in the art. The process of the invention may further comprise continuously recycling a portion of the product effluent to the hydrogenation zone. For example, the product effluent can be cooled, the tetraalkylcyclobutanediol and any solvent present can be condensed and purified, and any unreacted tetraalkylcyclobutanedione and hydrogen gas recycled to the hydrogenation zone. Purification of the tetraalkylcyclobutanediol hydrogenation product typically can be accomplished by conventional distillation or crystallization procedures. For example, where the hydrogenation product comprises 2,2,4,4-tetramethylcyclobutanediol, the solvent may be removed as a vapor in a first distillation and then low boiling by-products such as 2,2,4-trimethyl-3-oxo-1-pentanol may be vaporized from the diol product in a second distillation. Finally, the product diol may be distilled, optionally under reduced pressure, to obtain substantially pure 2,2,4,4-tetramethylcyclobutanediol.

Our process can be illustrated with particular reference to the preparation of 2,2,4,4-tetramethylcyclobutanediol by hydrogenation of 2,2,4,4-tetramethylcyclobutanedione in the gas phase. Another embodiment of our invention, therefore, is a process for the preparation of 2,2,4,4-tetramethylcyclobutane-1,3-diol, comprising:

I. continuously feeding to a hydrogenation zone hydrogen and a hydrogenatable reactant comprising 2,2,4,4-tetramethylcyclobutane-1,3-dione wherein the hydrogen and hydrogenatable reactant are in the gas phase;

II. continuously contacting the hydrogen and hydrogenatable reactant of step (I) at a temperature of about 100 to about 200° C. and a pressure of about 7 to about 28 bar with a catalyst comprising about 1 to about 8 weight percent ruthenium, based on the total weight of the catalyst, deposited on a support, to form a hydrogenation product comprising 2,2,4,4-tetramethylcyclobutane-1,3-diol having a cis:trans ratio of about 1:1 to about 1.6:1, wherein the temperature is greater than the dew point of the hydrogenation product;

III. continuously recovering from the reaction zone a gaseous effluent comprising the hydrogenation product; and IV. continuously recycling a portion of the gaseous effluent to the hydrogenation zone.

It will be apparent to persons skilled in the art that the various embodiments of cis:trans isomer ratios, dew points, catalyst metal, catalyst support, reaction conditions of temperature and pressure, feed ratios, purification and recycling of product effluent, and solvents described hereinabove are also application to the above process.

For example, the hydrogenatable reactant may further comprise at least one non-protic solvent. In another example, the support can comprise activated carbon, alumina, carbon nanotubes, or graphitized carbon and the non-protic solvent can be selected from hexane, heptane, cyclohexane, octane, diethyl ether, diisopropyl ether, tetrahydrofuran, methyl tert-butyl ether, ethyl acetate, n-propyl acetate, isopropyl isobutyrate, isobutyl propionate, octyl acetate, methyl butyrate, isobutyl isobutyrate, and isobutyl acetate. In one embodiment, for example, the solvent can comprise tetrahydrofuran.

In another embodiment, the catalyst can comprise ruthenium deposited on activated carbon, carbonized phenol formaldehyde resin particles, carbonized polysulfonated vinylaromatic polymer particles, graphitized carbon, or combinations thereof. Thus, another embodiment of our invention is a process for the preparation of 2,2,4,4-tetramethylcyclobutane-1,3-diol, comprising:

I. continuously feeding to a hydrogenation zone hydrogen and a hydrogenatable reactant comprising 2,2,4,4-tetramethylcyclobutane-1,3-dione at a hydrogen: 2,2,4,4-tetramethylcyclobutane-1,3-dione molar ratio of about 100:1 to about 500:1, wherein the hydrogen and hydrogenatable reactant are in the gas phase;

II. continuously contacting the hydrogen and hydrogenatable reactant of step (I) at a temperature of about 100 to about 160° C. and a pressure of about 14 to about 21 bars with a catalyst comprising about 1 to about 8 weight percent ruthenium, based on the total weight of the catalyst, deposited on a support comprising activated carbon, carbonized phenol formaldehyde resin particles, carbonized polysulfonated vinylaromatic polymer particles, graphitized carbon, or combinations thereof, to form a hydrogenation product comprising 2,2,4,4-tetramethylcyclobutane-1,3-diol having a cis:trans ratio of about 1:1 to about 1.6:1, wherein the temperature is greater than the dew point of the hydrogenation product; and III. continuously recovering from the reaction zone a gaseous effluent comprising the hydrogenation product.

The above process is understood to include the various embodiments of cis:trans isomer ratios, dew points, catalyst metal, catalyst support, reaction conditions of temperature and pressure, feed ratios, purification and recycling product effluent, and solvents described above. For example, the hydrogenatable reactant may further comprise at least one non-protic solvent selected from hexane, heptane, cyclohexane, octane, diethyl ether, diisopropyl ether, tetrahydrofuran, methyl tert-butyl ether, ethyl acetate, n-propyl acetate, isopropyl isobutyrate, isobutyl propionate, octyl acetate, methyl butyrate, isobutyl isobutyrate, and isobutyl acetate. In one embodiment, for example, the solvent can comprise tetrahydrofuran.

Embodiment A is a process for the preparation of a 2,2,4,4-tetraalkylcyclobutane-1,3-diol, comprising:

I. continuously feeding to a hydrogenation zone hydrogen and a hydrogenatable reactant comprising a 2,2,4,4-tetraalkylcyclobutane-1,3-dione having the formula (I):

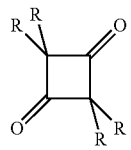

wherein the hydrogen and hydrogenatable reactant are in the gas phase and R is a alkyl radical containing 1 to 8 carbon atoms;

II. continuously contacting the hydrogen and hydrogenatable reactant of step (I) under hydrogenation conditions of temperature and pressure with a catalyst comprising nickel, ruthenium, or combination thereof, to form a hydrogenation product comprising a 2,2,4,4-tetraalkylcyclobutane-1,3-diol having the formula (II):

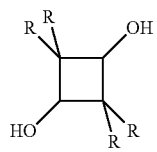

wherein the temperature is greater than the dew point of the hydrogenation product; and III. continuously recovering from the hydrogenation zone a gaseous effluent comprising the hydrogenation product.

The process of Embodiment A in which R is methyl, ethyl, propyl, isopropyl, butyl, isobutyl, pentyl, isoamyl, hexyl, heptyl, or octyl.

The process of Embodiment A or Embodiment A with any of the intervening features in which R is methyl.

The process of Embodiment A or Embodiment A with any of the intervening features in which the catalyst comprises metallic nickel or metallic ruthenium.

The process of Embodiment A or Embodiment A with any of the intervening features in which the catalyst comprises about 0.01 to about 10 weight percent ruthenium or about 0.01 to about 80 weight percent nickel, based on the total weight of the catalyst, deposited on a support comprising silica-alumina, titania, alumina-clay, clay, graphite, silicon carbide, zirconium, activated carbon, carbonized phenol formaldehyde resin particles, carbonized polysulfonated vinylaromatic polymer particles, or combinations thereof.

The process of Embodiment A or Embodiment A with any of the intervening features in which the catalyst comprises about 0.01 to about 10 weight percent ruthenium or about 0.01 to about 80 weight percent nickel, based on the total weight of the catalyst, deposited on a support comprising carbon nanotubes or graphitized carbon.

The process of Embodiment A or Embodiment A with any of the intervening features in which the hydrogen and hydrogenatable reactant are fed to the hydrogenation zone in a ratio of about 100:1 to about 1000:1

The process of Embodiment A or Embodiment A with any of the intervening features in which the hydrogenatable reactant is fed to the hydrogenation zone at a liquid-hourly space velocity of about 0.05 to about 4 hr$^{-1}$, the temperature is about 100 to about 180° C., and the pressure is about 7 to about 28 bars absolute.

The process of Embodiment A or Embodiment A with any of the intervening features in which the hydrogenatable reactant further comprises at least one solvent selected from water, alcohols, ethers, glycols, glycol ethers, alkanes, esters and mixtures thereof.

The process of Embodiment A or Embodiment A with any of the intervening features in which the solvent is selected from water methanol, ethanol, propanol, 1-butanol, 2-butanol, 2-ethylhexanol, 2,2-dimethyl-1,3-propanediol, ethylene glycol, diethylene glycol, triethylene glycol, propylene glycol, 1,4-butanediol, 2,2,4,4-tetramethylcyclobutane-1,3-diol, cyclohexanol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, methyl butyrate, and isobutyl acetate.

The process of Embodiment A or Embodiment A with any of the intervening features in which the 2,2,4,4-tetraalkylcyclobutane-1,3-diol comprises 2,2,4,4-tetramethylcyclobutane-1,3-diol having a cis:trans molar ratio of about 0.7:1 to about 1.7:1.

The process of Embodiment A or Embodiment A with any of the intervening features in which the reaction zone comprises a tubular or fluidized bed reactor.

The process of Embodiment A or Embodiment A with any of the intervening features further comprising (IV) continuously recycling a portion of the gaseous effluent to the hydrogenation zone.

Embodiment B is the process of Embodiment A in which the hydrogenatable reactant comprises 2,2,4,4-tetramethylcyclobutane-1,3-dione, the hydrogen and hydrogenatable reactant of step (I) are contacted at a temperature of about 100 to about 200° C. and a pressure of about 7 to about 28 bar with a catalyst comprising about 1 to about 8 weight percent ruthenium, based on the total weight of the catalyst, deposited on a support comprising activated carbon, alumina, carbon nanotubes, or graphitized carbon, to form a hydrogenation product comprising 2,2,4,4-tetramethylcyclobutane-1,3-diol having a cis:trans ratio of about 1:1 to about 1.6:1.

The process of Embodiment B in which the hydrogenatable reactant is fed into the hydrogenation zone at a hydrogen:2,2,4,4-tetramethylcyclobutane-1,3-dione molar ratio of about 100:1 to about 500:1 at temperature is about 100 to about 160° C. and a pressure of about 14 to about 21 bars, and further comprising continuously recovering from the hydrogenation zone a gaseous effluent comprising the hydrogenation product.

The process of the invention are further described and illustrated by the following examples.

EXAMPLES

General

The following is a general description of the reactor system and analytical methods used henceforward in Examples 1-5 unless otherwise specified. The reactor was constructed entirely of HASTELLOY™ C alloy. Reactants entered the base of the reactor via a 0.375 inch (9.5 mm) outer diameter (O.D.) inlet tube having a wall thickness of 0.065 inch (1.65 mm). The portion above the inlet tube expanded as a collar piece as a cone into a cylindrical section having a 0.625-inch (1.6 cm) inner diameter (I.D.) and a wall thickness of 0.1875 inch (4.8 mm) with overall length of 2.00 inches (5.1 cm). The top 0.38-inch (9.7 mm) portion of the collar was machined to a diameter of 0.750 inch (1.9 cm). The machined portion of the collar contained a 0.735-inch (1.87 cm) diameter by 0.0625-inch (1.65 mm) thick HASTELLOY™ C alloy 5 micron metal filter, which acted as a gas dispersion device and support for the catalyst. The filter and the collar containing the filter were welded to a 6.25-inch (15.9 cm) long by 0.625-inch (1.6 cm) I.D./0.750-inch (1.9 cm) O.D. HASTELLOY™ C alloy reaction tube. The reaction tube was welded to an expanded zone increasing in a conical fashion at 45 degrees to an outer diameter of 1.50 inches (3.81 cm), continuing in a cylindrical fashion for another 1.83 inches (4.65 cm) and then decreasing at a 45-degree angle and welded to a 4.50 inch (11.4 cm) long by 0.375-inch (9.5 mm) O.D. loading and sensing tube. The vertical loading and sensing tube contained a 0.375-inch (9.5 mm) O.D. pressure transducer side arm located 2.0 inches (5.1 cm) above the expanded zone and positioned at 45 degrees from vertical of the loading and sensing tube. Vapor product was removed from the expanded zone through a 0.250 inch (6.36 mm) O.D. product removal line connected approximately half the vertical distance of the expanded zone. The product removal line exited the reactor horizontally and then bent downward.

Metered gas flows were maintained by Brooks 5850 Series E mass flow controllers interfaced with a CAMILE™ 3300 Process Monitoring and Control System. Temperature control was also provided by the CAMILE™ 3300 Process Monitoring and Control System. Liquid feed was provided by an Alltech 301 HPLC pump. Liquid and gas feeds were vaporized by feeding to a heated HASTELLOY™ C alloy vaporizer maintained at 150° C. and transported in the vapor phase through a transfer line at 150° C. to the base of the reactor inlet tube. Heat to the reactor was provided by three separate split aluminum blocks with each split aluminum block surrounded by band heaters. Each split aluminum block heating unit had its own temperature control provided by the CAMILE™ 3300 Process Monitoring and Control System. The bottom heater provided heat to the reactor inlet tube and collar piece. The central heater provided heat to the reaction tube section. The top heated provided heat to the expansion zone.

The end of the product removal line was connected to a 50 micron filter attached to a HASTELLOY™ C alloy condenser, which was attached to a HASTELLOY™ C alloy product collection tank with a working capacity of one liter. The pressure was maintained using a Tescom Model 44-2300 backpressure regulator attached to a vent line on the top of product collection tank. Liquid samples were collected from a valve at the base of the liquid collection tank. Liquid products from the collection tank were weighed and analyzed by gas chromatography using a Hewlett Packard Model 5890A gas chromatograph fitted with a 30 m×0.25 mm DB-17 capillary column (0.25 micron film thickness) programmed at 90° C. for 2 minutes, 8° C./minute to 140° C. and holding at 140° C. for 5 minutes, 40° C./minute to 250° C. and holding at 250° C. for 5 minutes using a FID detector held at 250° C. (injector temperature=250° C.). The conversion, selectivity, yield, and the cis:trans ratio of the 2,2,4,4-tetramethylcyclobutane-1,3-diol product were calculated on the basis of GC area percentages. The percent 2,2,4,4-tetramethylcyclobutane-1,3-dione ("Dione") conversion was determined by the following formula:

$$\% \text{ Dione conversion} = 100 \times \frac{(\text{moles Dione fed into the reactor} - \text{moles unreacted Dione})}{\text{moles Dione fed into the reactor}}$$

The following abbreviations are used in the Tables. "TMCB" is 2,2,4,4-tetramethylcyclobutane-1,3-dione. "Ring-opened Ketol" is 1-hydroxy-2,2,4-trimethyl-3-pentanone, a product of the partial hydrogenation and ring opening of 2,2,4,4-tetramethylcyclobutane-1,3-dione. "Cyclic Ketol" is 3-hydroxy-2,2,4,4-tetramethylcyclobutanone, a product of the partial hydrogenation of 2,2,4,4-tetramethylcyclobutane-1,3-dione. "TMPD" is 2,2,4-trimethyl-1,3-pentanediol, a production of hydrogenation of 1-hydroxy-2,2,4-trimethyl-3-pentanone. "Cis-Diol" is cis-2,2,4,4-tetramethylcyclobutane-1,3-diol. "Trans-Diol" is trans-2,2,4,4-tetramethylcyclobutane-1,3-diol. "DIPK" is diisopropyl ketone. "DIPA" is diisopropyl carbinol.

The sample time shown in the tables, in hours, is the liquid sample collection time either from the start of the reaction, as in sample 1, or from the end of the previous sample. Pressures are reported in bars gauge (barg) unless otherwise indicated. Catalyst surface areas were measured volumetrically using the Brunauer-Emmett-Teller (BET) method.

Example 1

This example illustrates the hydrogenation of 2,2,4,4-tetramethylcyclobutane-1,3-dione in the presence of a catalyst containing 43 weight percent Ni on an alumina support (surface area=175 m$^2$/g, purchased from Engelhard, now BASF Catalysts, under the designation "E-235TR") at elevated pressure utilizing the process of the invention. The reactor was loaded with the 8.565 g of 20-40 mesh Ni/Al$_2$O$_3$ catalyst through the top of the reactor with hydrogen flowing at 500 standard cubic centimeters per minute (SCCM) through the base of the reactor. Hydrogen flows were maintained until the catalyst was removed from the reactor. A HASTELLOY™ C alloy thermowell extending from the top of the reactor to the bottom 5-micron sintered HASTELLOY™ C alloy filter was attached to the top of the vertical loading and sensing tube, and a pressure transducer was attached to the pressure transducer side arm. The system was pressurized to 20.7 bar gauge (300 psig) with 500 SCCM H$_2$. The three reactor heaters were set for 150° C. A solution consisting of 2,2,4,4-tetramethylcyclobutane-1,3-dione/THF in a weight ratio of 25/534.5 was fed to the reactor system at 0.479 ml/minute. The result is reported as E1-1 in Table 1. The hydrogenation of 2,2,4,4-tetramethylcyclobutane-1,3-dione over a range of flow rates, pressures and temperatures are reported as E1-2 to E1-24 in Tables 1A-1C.

TABLE 1A

| Example | E1-1 | E1-2 | E1-3 | E1-4 | E1-5 | E1-6 | E1-7 | E1-8 |
|---|---|---|---|---|---|---|---|---|
| React. condition | | | | | | | | |
| Temperature (° C.) | 150 | 150 | 150 | 150 | 140 | 140 | 140 | 140 |
| Pressure (barg) | 20.7 | 20.7 | 20.7 | 20.7 | 20.7 | 20.7 | 20.7 | 20.7 |
| H$_2$ flow rate (SCCM) | 500 | 658 | 658 | 658 | 658 | 658 | 658 | 1135 |
| Molar ratio of H$_2$:TMCB | 157.4 | 201.8 | 201.8 | 201.8 | 201.8 | 201.8 | 201.8 | 348 |

TABLE 1A-continued

| Example | E1-1 | E1-2 | E1-3 | E1-4 | E1-5 | E1-6 | E1-7 | E1-8 |
|---|---|---|---|---|---|---|---|---|
| Time on stream (hr) | 2 h | 4 h | 6 h | 8 h | 11 h | 13 h | 15 h | 17 h |
| TMCB conv. (%) | 100.00 | 100.00 | 100.00 | 100.00 | 100.00 | 100.00 | 100.00 | 99.98 |
| Selectivity (%) | | | | | | | | |
| DIPK | 4.07 | 3.59 | 2.52 | 3.71 | 3.49 | 1.54 | 1.88 | 1.53 |
| DIPA | 59.30 | 17.32 | 21.74 | 11.67 | 6.98 | 6.91 | 4.14 | 2.04 |
| Ring-opened ketol | 6.40 | 12.09 | 10.07 | 13.53 | 14.34 | 11.32 | 13.53 | 12.50 |
| Cyclic ketol | 0.00 | 0.00 | 0.00 | 0.00 | 0.00 | 0.00 | 0.00 | 1.53 |
| Cis-Diol | 2.33 | 6.21 | 3.66 | 7.96 | 13.57 | 12.86 | 21.43 | 29.08 |
| Trans-Diol | 1.74 | 4.58 | 2.75 | 5.57 | 10.08 | 9.40 | 16.92 | 22.70 |
| TMPD | 26.16 | 56.21 | 59.27 | 57.56 | 51.55 | 57.97 | 42.11 | 30.61 |
| Ratio of cis/trans | 1.33 | 1.36 | 1.33 | 1.43 | 1.35 | 1.37 | 1.27 | 1.28 |

TABLE 1B

| Example | E1-9 | E1-10 | E1-11 | E1-12 | E1-13 | E1-14 | E1-15 | E1-16 | E1-17 |
|---|---|---|---|---|---|---|---|---|---|
| React. condition | | | | | | | | | |
| Temperature (° C.) | 140 | 130 | 130 | 130 | 130 | 130 | 130 | 130 | 130 |
| Pressure (bar) | 20.7 | 20.7 | 20.7 | 20.7 | 6.9 | 6.9 | 6.9 | 6.9 | 6.9 |
| $H_2$ flow rate (SCCM) | 1135 | 1982 | 1982 | 1982 | 500 | 500 | 500 | 500 | 1982 |
| Molar ratio of $H_2$:TMCB | 348 | 607 | 607 | 607 | 157.4 | 157.4 | 157.4 | 157.4 | 607 |
| Time on stream (hr) | 19 | 21 | 23 | 24.2 | 26.1 | 28.1 | 30.1 | 32.1 | 34.1 |
| TMCB conv. (%) | 99.98 | 99.97 | 99.78 | 99.72 | 99.51 | 99.90 | 99.99 | 100.00 | 100.00 |
| Selectivity (%) | | | | | | | | | |
| DIPK | 1.39 | 0.88 | 0.86 | 1.42 | 4.90 | 2.07 | 4.36 | 3.80 | 1.44 |
| DIPA | 1.39 | 5.41 | 1.37 | 0.63 | 1.34 | 2.16 | 1.24 | 0.80 | 0.89 |
| Ring-opened ketol | 11.78 | 10.50 | 12.35 | 18.77 | 31.35 | 19.33 | 29.88 | 33.40 | 20.22 |
| Cyclic ketol | 0.00 | 0.00 | 0.00 | 0.00 | 0.00 | 0.00 | 0.00 | 0.00 | 0.00 |
| Cis-Diol | 32.56 | 18.12 | 24.36 | 27.44 | 22.73 | 13.63 | 15.56 | 16.80 | 24.35 |
| Trans-Diol | 25.17 | 14.03 | 20.58 | 23.50 | 18.72 | 10.09 | 11.20 | 12.00 | 17.19 |
| TMPD | 27.71 | 51.05 | 40.48 | 28.23 | 20.95 | 52.72 | 37.76 | 33.20 | 35.90 |
| Ratio of cis/trans | 1.29 | 1.29 | 1.18 | 1.17 | 1.21 | 1.35 | 1.39 | 1.40 | 1.42 |

TABLE 1C

| Example | E1-18 | E1-19 | E1-20 | E1-21 | E1-22 | E1-23 | E1-24 |
|---|---|---|---|---|---|---|---|
| React. condition | | | | | | | |
| Temperature (° C.) | 130 | 130 | 130 | 140 | 140 | 140 | 140 |
| Pressure (bar) | 6.9 | 6.9 | 6.9 | 6.9 | 6.9 | 6.9 | 6.9 |
| $H_2$ flow rate (SCCM) | 1982 | 1982 | 1982 | 1982 | 1982 | 1982 | 1982 |
| Molar ratio of $H_2$:TMCB | 607 | 607 | 607 | 607 | 607 | 607 | 607 |
| Time on stream (hr) | 36.1 | 38.1 | 40.1 | 42.1 | 44.1 | 46.1 | 48.1 |
| TMCB conv. (%) | 100.00 | 100.00 | 100.00 | 100.00 | 100.00 | 100.00 | 100.00 |
| Selectivity (%) | | | | | | | |
| DIPK | 2.75 | 3.42 | 3.94 | 6.36 | 7.23 | 8.38 | 8.74 |
| DIPA | 0.80 | 0.94 | 1.11 | 6.00 | 5.42 | 6.15 | 6.32 |
| Ring-opened ketol | 21.90 | 23.73 | 24.97 | 23.13 | 22.17 | 22.12 | 22.58 |
| Cyclic ketol | 0.00 | 0.00 | 0.00 | 0.00 | 0.00 | 0.00 | 0.00 |
| Cis-Diol | 26.15 | 24.79 | 23.12 | 16.28 | 11.08 | 9.29 | 8.74 |
| Trans-Diol | 18.69 | 17.36 | 15.87 | 10.16 | 7.11 | 6.28 | 5.91 |
| TMPD | 29.70 | 29.75 | 31.00 | 38.07 | 46.99 | 47.77 | 47.72 |
| Ratio of cis/trans | 1.40 | 1.43 | 1.46 | 1.60 | 1.56 | 1.48 | 1.48 |

Example 2

This example illustrates the hydrogenation of 2,2,4,4-tetramethylcyclobutane-1,3-dione in the presence of prereduced Ru on carbon at elevated pressure utilizing the process of the invention. The reactor was loaded with 3.609 g of a pre-reduced, 20-40 mesh, 7 wt % Ru on graphitized carbon (surface area=528 m²/g, purchased from Engelhard, now BASF Catalysts, under the designation "C3610") through the top of the reactor. The in-situ prereduction with hydrogen was carried as follows: the catalyst was swept with nitrogen at a flow rate of 500 SCCM at room temperature for 2 hours. The catalyst was then reduced with 50 volume % hydrogen in nitrogen at 150° C. for 2.5 hours and then 180° C. for 2 hours. The prereduced catalyst was cooled overnight under nitrogen. The following morning, the three reactor heaters were set for 130-140° C. with hydrogen flowing at 1135 standard cubic centimeters per minute (SCCM) through the base of the reactor. The system was pressurized to 20.7 barg (300 psig) with 1135 SCCM $H_2$. A solution consisting of 2,2,4,4-tetramethylcyclobutane-1,3-dione/methanol in a weight ratio of 25/534.5 was fed to the reactor system at 0.479 ml/minute. The results are reported in Table 2.

TABLE 2

| Example | E2-1 | E2-2 | E2-3 | E2-4 | E2-5 | E2-6 | E2-7 | E2-8 | E2-9 | E2-10 |
|---|---|---|---|---|---|---|---|---|---|---|
| React. condition | | | | | | | | | | |
| Temperature (° C.) | 140 | 140 | 140 | 135 | 135 | 135 | 135 | 130 | 130 | 130 |
| Pressure (barg) | 20.7 | 20.7 | 20.7 | 20.7 | 20.7 | 20.7 | 20.7 | 20.7 | 20.7 | 20.7 |
| $H_2$ fl. rate (SCCM) | 1135 | 1135 | 1135 | 1135 | 1135 | 1135 | 1135 | 1135 | 1135 | 1135 |
| Molar ratio of $H_2$:TMCB | 348 | 348 | 348 | 348 | 348 | 348 | 348 | 348 | 348 | 348 |
| Time on stream (hr) | 2 | 5 | 7 | 9 | 11 | 12 | 14 | 14.7 | 17.2 | 19.5 |
| TMCB conv. (%) | 100 | 100 | 100 | 100 | 100 | 100 | 100 | 100 | 100 | 100 |
| Selectivity (%) | | | | | | | | | | |
| DIPK | 0.19 | 0.17 | 0.17 | 0.24 | 0.21 | 0.49 | 0.73 | 0.83 | 0.88 | 1.94 |
| DIPA | 0.77 | 0.68 | 0.50 | 3.06 | 0.63 | 7.98 | 1.83 | 23.76 | 3.96 | 1.46 |
| Ring-opened ketol | 4.04 | 0.51 | 0.34 | 0.47 | 0.21 | 0.33 | 0.37 | 0.28 | 0.44 | 2.43 |
| Cyclic ketol | 0.00 | 0.00 | 0.00 | 0.00 | 0.00 | 0.00 | 0.00 | 0.00 | 0.00 | 0.00 |
| Cis-Diol | 45.58 | 55.03 | 55.70 | 54.59 | 56.70 | 51.30 | 54.58 | 40.61 | 53.74 | 51.94 |
| Trans-Diol | 33.27 | 40.20 | 40.60 | 39.53 | 40.59 | 37.62 | 40.66 | 31.77 | 39.21 | 41.26 |
| TMPD | 16.15 | 3.41 | 2.68 | 2.12 | 2.30 | 2.28 | 1.83 | 2.76 | 1.76 | 0.97 |
| Ratio of cis/trans | 1.37 | 1.37 | 1.37 | 1.38 | 1.38 | 1.36 | 1.34 | 1.28 | 1.37 | 1.26 |

Example 3

This example illustrates the hydrogenation of 2,2,4,4-tetramethylcyclobutane-1,3-dione in the presence of a prereduced Ni on $Al_2O_3$ catalyst at elevated pressure utilizing the process of the invention. The reactor was loaded with 8.983 g of a pre-reduced, 20-40 mesh, 60 wt % nickel on alumina catalyst (surface area=190-240 $m^2$/g, purchased from Südchemie under the designation "NiSAT-H") through the top of the reactor. The prereduction with hydrogen was carried out in-situ by sweeping the catalyst with nitrogen at a flow rate of 500 SCCM at room temperature for 2 hours. The catalyst was then reduced with 50 volume % hydrogen in nitrogen at 150° C. overnight and then 180° C. for 2 hours. The prereduced catalyst was cooled down under nitrogen. The three reactor heaters were then set for 130-140° C. with hydrogen flowing at 1135 standard cubic centimeters per minute (SCCM) through the base of the reactor. The system was pressurized to 300 psig (20.78 bars) with 1135 SCCM $H_2$. A solution consisting of 2,2,4,4-tetramethylcyclobutane-1,3-dione/THF in a weight ratio of 25/534.5 was fed to the reactor system at 0.479 ml/minute. The results are reported in Table 3.

TABLE 3

| Example | E3-1 | E3-2 | E3-3 | E3-4 | E3-5 |
|---|---|---|---|---|---|
| Reaction condition | | | | | |
| Temperature (° C.) | 140 | 140 | 140 | 130 | 130 |
| Pressure (barg) | 20.7 | 20.7 | 20.7 | 20.7 | 20.7 |
| $H_2$ flow rate (SCCM) | 1135 | 1135 | 1135 | 1135 | 1135 |
| Molar ratio of $H_2$:TMCB | 348 | 348 | 348 | 348 | 348 |
| Time on stream (hr) | 1.8 | 3.8 | 5.3 | 6.3 | 8.3 |
| TMCB conv. (%) | 100.00 | 100.00 | 100.00 | 100.00 | 100.00 |
| Selectivity (%) | | | | | |
| DIPK | 0.83 | 3.32 | 3.85 | 1.86 | 1.31 |
| DIPA | 14.29 | 20.30 | 8.79 | 4.65 | 9.19 |
| Ring-opened ketol | 0.41 | 7.75 | 11.81 | 9.30 | 8.44 |
| Cyclic ketol | 0.00 | 0.00 | 0.00 | 0.00 | 0.00 |
| Cis-Diol | 38.30 | 7.01 | 7.69 | 9.77 | 8.63 |
| Trans-Diol | 38.30 | 6.27 | 5.77 | 6.51 | 5.82 |
| TMPD | 7.87 | 55.35 | 62.09 | 67.91 | 66.60 |
| Ratio of cis/trans | 1.00 | 1.12 | 1.33 | 1.50 | 1.48 |

Example 4

This example illustrates the hydrogenation of 2,2,4,4-tetramethylcyclobutane-1,3-dione in the presence of a prereduced nickel on alumina catalyst at elevated pressure utilizing the process of the invention. The reactor was loaded with 8.264 g of a pre-reduced, 20-40 mesh catalyst containing 60 weight percent Ni on an alumina support (surface area=160 $m^2$/g, purchased from Engelhard, now BASF Catalysts, under the designation "Ni3288") through the top of the reactor. The in-situ prereduction with hydrogen was done as following: sweep the catalyst with nitrogen at a flow rate of 500 SCCM at room temperature for 2 hours. Then the catalyst was reduced with 50 volume % hydrogen in nitrogen at 150° C. for 2 hours and then 180° C. for 2 hours. The prereduced catalyst was cooled down under nitrogen. Then the three reactor heaters were set for 120-135° C. with hydrogen flowing at 1135 standard cubic centimeters per minute (SCCM) through the base of the reactor. The system was pressurized to 20.7 barg (300 psig) with 1135 SCCM $H_2$. A solution consisting of 2,2,4,4-tetramethylcyclobutane-1,3-dione/THF in a weight ratio of 25/534.5 was fed to the reactor system at 0.479 ml/minute. The results are reported in Table 4.

TABLE 4

| Example | E4-1 | E4-2 | E4-3 | E4-4 | E4-5 | E4-6 | E4-7 | E4-8 | E4-9 | E4-10 |
|---|---|---|---|---|---|---|---|---|---|---|
| React. cond. | | | | | | | | | | |
| Temp. (° C.) | 135 | 135 | 135 | 130 | 130 | 120 | 120 | 120 | 120 | 120 |
| Pressure (bar) | 20.7 | 20.7 | 20.7 | 20.7 | 20.7 | 20.7 | 20.7 | 20.7 | 20.7 | 20.7 |
| $H_2$ flow rate (SCCM) | 1135 | 1135 | 1135 | 1135 | 1135 | 1135 | 1135 | 1135 | 1135 | 1135 |
| Molar ratio of $H_2$:TMCB | 348 | 348 | 348 | 348 | 348 | 348 | 348 | 348 | 348 | 348 |
| Time on stream (hr) | 2 | 4.3 | 6.3 | 8.3 | 11.7 | 13.8 | 16.3 | 18.5 | 20.5 | 21.8 |
| TMCB conv. (%) | 100.00 | 100.00 | 100.00 | 100.00 | 100.00 | 100.00 | 100.00 | 100.00 | 100.00 | 100.00 |
| Selectivity (%) | | | | | | | | | | |
| DIPK | 0.00 | 3.85 | 3.96 | 3.20 | 3.36 | 2.34 | 1.61 | 2.93 | 4.51 | 8.03 |
| DIPA | 7.02 | 63.19 | 51.44 | 16.53 | 7.17 | 3.80 | 4.84 | 2.93 | 4.92 | 10.95 |
| Ring-opened ketol | 1.89 | 3.85 | 6.83 | 11.73 | 17.04 | 13.45 | 11.65 | 12.45 | 14.75 | 15.33 |
| Cyclic ketol | 0.00 | 0.00 | 0.00 | 0.00 | 0.00 | 0.00 | 0.00 | 0.00 | 0.00 | 0.00 |
| Cis-Diol | 11.36 | 1.10 | 0.72 | 4.80 | 10.31 | 16.67 | 9.86 | 22.34 | 32.38 | 28.47 |
| Trans-Diol | 7.85 | 1.10 | 0.72 | 3.20 | 7.40 | 11.99 | 6.81 | 16.48 | 24.59 | 21.90 |
| TMPD | 71.86 | 26.92 | 36.33 | 60.53 | 54.71 | 51.75 | 65.23 | 42.86 | 18.85 | 15.33 |
| Ratio of cis/trans | 1.45 | 1.00 | 1.00 | 1.50 | 1.39 | 1.39 | 1.45 | 1.36 | 1.32 | 1.30 |

Example 5

Steam-activated carbononized phenol-formaldehyde resin spheres (20 g) were placed in an evaporating dish and combined with a solution prepared from ruthenium nitrosyl nitrate containing 36.1 wt % Ru (3.88 g) and water (20 ml). The mixture was stirred until uniform and was evaporated on the steam bath with occasional stirring until the solids became free flowing. The Ru-impregnated, steam-activated catalyst was transferred to a quartz tube containing a quartz wool support plug. The quartz tube was placed into a LIND-BERG™ electric furnace and heated in an upward flow of nitrogen (100 SCCM) over a 2 hour period to 300° C. and held at 300° C. for 2 hours before cooling back to ambient temperature. The dried catalyst had a BET surface area of 1183 m²/g.

This example illustrates the hydrogenation of 2,2,4,4-tetramethylcyclobutane-1,3-dione in the presence of the prereduced Ru on carbonized phenol-formaldehyde resin spheres described above at elevated pressure utilizing the process of the invention. The reactor was loaded with 6.60 g of the 7 wt % Ru/C catalyst made above (20-40 mesh) through the top of the reactor. The prereduction with hydrogen was carried out in-situ by sweeping the catalyst with helium at a flow rate of 500 SCCM at room temperature overnight. The catalyst was then reduced with 50 volume % hydrogen in helium at 150° C. for 2 hours and at 180° C. for 2 hours. The prereduced catalyst was cooled under helium. The three reactor heaters were set for 130-140° C. with hydrogen flowing at 1135 standard cubic centimeters per minute (SCCM) through the base of the reactor. The system was pressurized to 20.7 barg (300 psig) with 1135 SCCM $H_2$ and a solution of 2,2,4,4-tetramethyl-cyclobutane-1,3-dione in THF in a weight ratio of 25/534.5 was fed to the reactor system at 0.479 ml/minute. The results are reported in Table 5.

TABLE 5

| Example | E5-1 | E5-2 | E5-3 | E5-4 | E5-5 | E5-6 | E5-7 | E5-8 | E5-9 |
|---|---|---|---|---|---|---|---|---|---|
| Reaction condition | | | | | | | | | |
| Temperature (° C.) | 135 | 135 | 135 | 135 | 130 | 130 | 140 | 140 | 140 |
| Pressure (bar) | 20.7 | 20.7 | 20.7 | 20.7 | 20.7 | 20.7 | 20.7 | 20.7 | 20.7 |
| $H_2$ flow rate (SCCM) | 1135 | 1135 | 1135 | 1135 | 1135 | 1135 | 1135 | 1135 | 1135 |
| Molar ratio of H2:TMCB | 348 | 348 | 348 | 348 | 348 | 348 | 348 | 348 | 348 |
| Time on stream (hr) | 5 | 9 | 11.8 | 13.4 | 17.4 | 19.4 | 23.4 | 25.4 | 27.4 |
| TMCB conv. (%) | 100.00 | 100.00 | 100.00 | 100.00 | 100.00 | 100.00 | 99.99 | 100.00 | 100.00 |
| Selectivity (%) | | | | | | | | | |
| DIPK | 0.98 | 1.10 | 0.54 | 0.79 | 0.74 | 1.08 | 1.62 | 0.62 | 1.67 |
| DIPA | 2.29 | 3.30 | 1.61 | 2.63 | 4.04 | 2.17 | 1.42 | 1.23 | 1.46 |
| Ring-opened ketol | 0.65 | 0.55 | 0.80 | 1.05 | 0.37 | 0.36 | 3.64 | 2.26 | 2.09 |
| Cyclic ketol | 1.96 | 1.92 | 1.88 | 2.11 | 1.47 | 1.81 | 3.04 | 3.29 | 3.14 |
| Cis-Diol | 51.63 | 50.82 | 51.47 | 49.74 | 52.21 | 52.35 | 47.77 | 48.87 | 48.12 |
| Trans-Diol | 38.56 | 38.46 | 38.87 | 37.63 | 38.60 | 39.35 | 35.83 | 37.58 | 37.45 |
| TMPD | 3.92 | 3.85 | 4.83 | 6.05 | 2.57 | 2.89 | 6.68 | 6.16 | 6.07 |
| Ratio of cis/trans | 1.34 | 1.32 | 1.32 | 1.32 | 1.35 | 1.33 | 1.33 | 1.30 | 1.28 |

Preparation of Ru/Carbon Nanotube Catalysts

This example illustrates a procedure for the preparation of a ruthenium on carbon nanotube catalyst by using a wet impregnation method. Carbon nanotube extrudates (20 g, 1/16", surface area=244 m$^2$/g, available from Hyperion Catalyst International, Inc) were charged to a 100 mL glass bottle, cooled in a dry ice batch, followed by 44 g of a 2% ruthenium acetoacetate solution in acetone added dropwise. The impregnated carbon nanotube extrudates were dried at ambient temperature for 4 hours and then in an oven at 120° C. for 2 hours. The dried extrudates were then loaded in a ½" stainless steel tube and exposed to 200 standard cubic centimeters per minute (SCCM) of 10% hydrogen in nitrogen at 180° C. for 2 hours. The nominal Ru loading was 3%.

Comparative Example 1

A mixture of 18 g of 2,2,4,4-tetramethylcyclobutane-1,3-dione, 160 g of isobutyl isobutyrate (IBIB), and 15 g of a catalyst containing 2 weight percent Ru on an α-alumina support and having a surface area of 40 m$^2$/g (obtained from BASF Catalysts), was charged to a 300 mL stainless steel autoclave. The catalyst was placed in a stainless steel catalyst basket within the autoclave. The autoclave was agitated and purged twice with nitrogen (0.069 MPa, 10 psig) at an ambient temperature and then purged with hydrogen (0.069 MPa, 10 psig). The autoclave was then heated to 130° C. and pressurized with hydrogen (2.76 MPa, 400 psig). After 2 hours, a product sample was taken and analyzed by gas chromatography (GC). The conversion of dione was 94% and the selectivity to diol was 41%. The cis:trans isomer ratio of the diol was 1.02.

Comparative Example 2

A pre-reduced catalyst (2.5 g) containing 7 weight percent Ru on a graphitized carbon support (purchased from Engelhard, now BASF Catalysts, under the designation "C3610") and having a surface area of 589 m$^2$/g was loaded in a 300 mL stainless steel autoclave in a stainless steel catalyst basket with 18 g of 2,2,4,4-tetramethylcyclobutane-1,3-dione and 160 g of isobutyl butyrate (IBIB). The autoclave was agitated and purged twice with nitrogen (0.069 MPa, 10 psig) at an ambient temperature and then purged with hydrogen (0.069 MPa, 10 psig). The autoclave was heated to 130° C. and pressurized with hydrogen (2.76 MPa, 400 psig). After 1 hour, a product sample was taken and analyzed by GC. The conversion of dione was 55% and the selectivity to diol was 29%. The cis:trans isomer ratio of the diol was 1.06.

Comparative Example 3

A 2 wt % Ru on silica catalyst (2.5 g, surface area=300 m$^2$/g, obtained from BASF Catalysts) was charged to a 300 mL stainless steel autoclave in a stainless steel catalyst basket, followed by 18 g of 2,2,4,4-tetramethylcyclobutane-1,3-dione and 160 g of IBIB. The autoclave was agitated and purged twice with nitrogen (0.069 MPa, 10 psig) at ambient temperature and then purged with hydrogen (0.069 MPa, 10 psig). The autoclave was heated to 130° C. and pressurized with hydrogen (2.76 MPa, 400 psig). After 1 hour, a product sample was taken and analyzed by GC. The conversion of dione was 52% and the selectivity to diol was 30%. The cis:trans isomer ratio of the diol was 1.06.

Comparative Example 4

A 3 wt % Ru on carbon nanotube catalyst (0.5 g, surface area=244 m$^2$/g) was loaded in a 100 mL stainless steel autoclave in a stainless steel catalyst basket with 6 g of 2,2,4,4-tetramethylcyclobutane-1,3-dione and 54 g of IBIB. The autoclave was agitated and purged twice with helium (0.69 MPa, 100 psig) at ambient temperature and then purged with hydrogen (0.69 MPa, 100 psig). The autoclave then was heated to 130° C. and pressurized with hydrogen (2.76 MPa, 400 psig). After 1 hour, a product sample was taken and analyzed by GC. The conversion of dione was 99.9% and the selectivity to diol was 91%. The cis:trans isomer ratio of the diol was 1.04.

Comparative Example 5

A 3 wt % Ru on carbon nanotube catalyst (0.5 g, surface area=244 m$^2$/g) was loaded in a 100 mL stainless steel autoclave in a stainless steel catalyst basket with 6 g of 2,2,4,4-tetramethylcyclobutane-1,3-dione and 54 g of IBIB. The autoclave was agitated and purged twice with helium (0.69 MPa, 100 psig) at ambient temperature and then purged with hydrogen (0.69 MPa, 100 psig). The autoclave was then heated to 140° C. and pressurized with hydrogen (2.76 MPa, 400 psig). After 1 hour, a product sample was taken and analyzed by GC. The conversion of dione was 100% and the selectivity to diol was 87%. The cis:trans isomer ratio of the diol was 1.08.

Comparative Example 6

A 3 wt % Ru on carbon nanotube catalyst (0.5 g, surface area=244 m$^2$/g) was loaded in a 100 mL stainless steel autoclave in a stainless steel catalyst basket with 6 g of 2,2,4,4-tetramethylcyclobutane-1,3-dione and 54 g of IBIB. The autoclave was agitated and purged twice with helium (0.69 MPa, 100 psig) at ambient temperature and then purged with hydrogen (0.69 MPa, 100 psig). The autoclave was then heated to 120° C. and pressurized with hydrogen (2.76 MPa, 400 psig). After 1 hour, a product sample was taken and analyzed by GC. The conversion of dione was 99.9% and selectivity to diol was 94%. The cis:trans isomer ratio of the diol was 1.07.

Comparative Example 7

This example followed a similar procedure to Example 1 of U.S. Pat. No. 2,936,324 using 5 weight percent Ru on activated carbon catalyst, except that a higher temperature and lower pressure was used. A 5 wt % Ru on carbon powder catalyst (obtained from Engelhard, now BASF Catalysts, surface area=881 m$^2$/g) was dried in a conventional oven at 105° C. overnight. The dried catalyst (1.33 g) was loaded in a 100 mL stainless steel autoclave reactor. The autoclave was purged twice with helium (0.69 MPa, 100 psig) and then with hydrogen at ambient temperature. After the autoclave was heated to 150° C. and the reactor pressure was increased to 2.76 MPa (400 psig) with hydrogen. After 1 hour, the reactor was cooled to about 50° C. and 26.7 g of 2,2,4,4-tetramethylcyclobutane-1,3-dione and 66.7 g of methanol were added. The autoclave was agitated and purged twice with helium (0.69 MPa, 100 psig) and then with hydrogen (0.69 MPa, 100 psig). The autoclave was then heated to 140° C. and pressurized to 2.76 MPa (400 psig). After 1 hour, a product sample was taken and analyzed by GC. The conversion of dione was 99.7% and the selectivity to diol was 85.8%. The cis:trans isomer ratio of the diol was 0.84.

Comparative Example 8

Ru powder (0.1 g, purchased from Aldrich Chemical Co.) was loaded in a 100 mL stainless steel autoclave reactor with 64 g of IBIB. the autoclave was agitated and purged twice with helium (0.69 MPa, 100 psig) and then with hydrogen at ambient temperature. The autoclave was heated to 150° C. and the reactor pressure was increased to (2.76 MPa, 400 psig) with hydrogen. After the 1 hour, the reactor was cooled down to approximately 50° C., and 6 g of 2,2,4,4-tetramethylcyclobutane-1,3-dione were added to the autoclave reactor. The autoclave was agitated and purged twice with helium (0.69 MPa, 100 psig) followed by hydrogen. The autoclave was then heated to 140° C. and pressurized to 2.76 MPa (400 psig). After 1 hour, a product sample was taken and analyzed. The conversion of dione was 99.8% and the yield of diol was 59.5%. The cis:trans isomer ratio of the diol was 1.11.

Comparative Example 9

A catalyst (2.5 g) containing 7 weight percent Ru on a graphitized carbon support (purchased from Engelhard, now BASF Catalysts, under the designation "C3610") and having a surface area of 589 m²/g was loaded in a 300 mL stainless steel autoclave in a stainless steel catalyst basket with 28 g of 2,2,4,4-tetramethylcyclobutane-1,3-dione and 160 g of THF. The autoclave was agitated and purged twice with nitrogen (3.45 MPa, 500 psig) at an ambient temperature and then purged with hydrogen (0.69 MPa, 100 psig). Then, the autoclave was heated to 130° C. and pressurized with hydrogen (2.76 MPa, 400 psig). After 1 hour, a product sample was taken and analyzed by GC. The conversion of dione was 99% and the selectivity to diol was 58%. The cis:trans isomer ratio of the diol was 1.06.

Comparative Example 10

A catalyst (701.3 g) containing 60 weight percent Ni on an alumina support (purchased from Engelhard, now BASF Catalysts, under the designation "Ni3288") and having a surface area of 160 m²/g was loaded in a trickle bed reactor. The reactor was pressurized to 1000 psig (6.90 MPa) with H₂ and heated up to 170° C. A solution consisting of 20 wt % of 2,2,4,4-tetramethylcyclobutane-1,3-dione in isobutyl acetate was fed to the reactor at 93 g/minute. After 3 hours, three product samples were taken with increment of 0.5 hr and analyzed by GC. The average conversion of dione was 100% and selectivity to diol was 80%. The average of cis:trans isomer ratio of the diol was 1.16.

Comparative Example 11

A catalyst (759.7 g) containing 43 weight percent Ni on an alumina support (purchased from Engelhard, now BASF Catalysts, under the designation "E-235TR") and having a surface area of 175 m2/g was loaded in a trickle bed reactor. The reactor was pressurized to 500 psig (3.45 MPa) with H2 and heated up to 170° C. A solution consisting of 25 wt % of 2,2,4,4-tetramethylcyclobutane-1,3-dione in isobutyl acetate was fed to the reactor at 96 g/minute. After 1.5 hours, three product samples were taken with increment of 0.5 hr and analyzed by GC. The average conversion of dione was 100% and selectivity to diol was 84%. The average of cis:trans isomer ratio of the diol was 0.98.

We claim:
1. A process for the preparation of a 2,2,4,4-tetraalkylcyclobutane-1,3-diol, comprising:
(A) continuously feeding to a hydrogenation zone hydrogen and a hydrogenatable reactant comprising a 2,2,4,4-tetraalkylcyclobutane-1,3-dione having the formula (I):

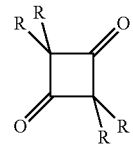

wherein the hydrogen and hydrogenatable reactant are in the gas phase and R is a alkyl radical containing 1 to 8 carbon atoms;
(B) continuously contacting the hydrogen and hydrogenatable reactant of step (A) under hydrogenation conditions of temperature and pressure with a catalyst comprising nickel, ruthenium, or combination thereof, to form a hydrogenation product comprising a 2,2,4,4-tetraalkylcyclobutane-1,3-diol having the formula (II):

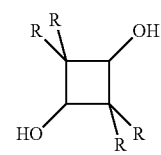

wherein the temperature is greater than the dew point of the hydrogenation product; and
(C) continuously recovering from the hydrogenation zone a gaseous effluent comprising the hydrogenation product.
2. The process according to claim 1 wherein R is methyl, ethyl, propyl, butyl, pentyl, hexyl, heptyl, or octyl.
3. The process according to claim 2 wherein R is methyl.
4. The process according to claim 3 wherein the catalyst comprises metallic nickel or metallic ruthenium.
5. The process according to claim 3 wherein the catalyst comprises about 0.01 to about 10 weight percent ruthenium or about 0.01 to about 80 weight percent nickel, based on the total weight of the catalyst, deposited on a support comprising silica-alumina, titania, alumina-clay, clay, graphite, silicon carbide, zirconium, activated carbon, carbonized phenol formaldehyde resin particles, carbonized polysulfonated vinylaromatic polymer particles, carbon nanotubes, graphitized carbon, or combinations thereof.
6. The process according to claim 5 wherein the support comprises carbon nanotubes or graphitized carbon.
7. The process according to claim 3 wherein the hydrogen and hydrogenatable reactant are fed to the hydrogenation zone in a ratio of about 100:1 to about 1000:1.
8. The process according to claim 3 wherein the hydrogenatable reactant is fed to the hydrogenation zone at a liquid-hourly space velocity of about 0.05 to about 4 hr⁻¹, the temperature is about 100 to about 180° C., and the pressure is about 7 to about 28 bars absolute.
9. The process according to claim 3 wherein the hydrogenatable reactant further comprises at least one solvent selected from the group consisting of water, alcohols, ethers, glycols, glycol ethers, alkanes, esters, and mixtures thereof.
10. The process according to claim 9 wherein the solvent is selected from the group consisting of water methanol, ethanol, propanol, 1-butanol, 2-butanol, 2-ethylhexanol, 2,2-dimethyl-1,3-propanediol, ethylene glycol, diethylene glycol, triethylene glycol, propylene glycol, 1,4-butanediol, 2,2,4,4-tetramethylcyclobutane-1,3-diol, cyclohexanol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, methyl butyrate, isobutyl acetate, and mixtures thereof.

11. The process according to claim 1 wherein the 2,2,4,4-tetraalkylcyclobutane-1,3-diol comprises 2,2,4,4-tetramethylcyclobutane-1,3-diol having a cis:trans molar ratio of about 0.7:1 to about 1.7:1.

12. The process according to claim 1 wherein the reaction zone comprises a tubular or fluidized bed reactor.

13. The process according to claim 1 further comprising step (D), continuously recycling a portion of the gaseous effluent to the hydrogenation zone.

14. A process for the preparation of 2,2,4,4-tetramethylcyclobutane-1,3-diol, comprising:
(A) continuously feeding to a hydrogenation zone hydrogen and a hydrogenatable reactant comprising 2,2,4,4-tetramethylcyclobutane-1,3-dione
wherein the hydrogen and hydrogenatable reactant are in the gas phase;
(B) continuously contacting the hydrogen and hydrogenatable reactant of step (A) at a temperature of about 100 to about 200° C. and a pressure of about 7 to about 28 bar with a catalyst comprising about 1 to about 8 weight percent ruthenium, based on the total weight of the catalyst, deposited on a support, to form a hydrogenation product comprising 2,2,4,4-tetramethylcyclobutane-1,3-diol having a cis:trans ratio of about 1:1 to about 1.6:1, wherein the temperature is greater than the dew point of the hydrogenation product;
(C) continuously recovering from the hydrogenation zone a gaseous effluent comprising the hydrogenation product; and
(D) continuously recycling a portion of the gaseous effluent to the hydrogenation zone.

15. The process according to claim 14 wherein the hydrogenatable reactant further comprises at least one non-protic solvent.

16. The process according to claim 15 wherein the support comprises activated carbon, alumina, carbon nanotubes, or graphitized carbon and the non-protic solvent is selected from the group consisting of hexane, heptane, cyclohexane, octane, diethyl ether, diisopropyl ether, tetrahydrofuran, methyl tert-butyl ether, ethyl acetate, n-propyl acetate, isopropyl isobutyrate, isobutyl propionate, octyl acetate, methyl butyrate, isobutyl isobutyrate, and isobutyl acetate.

17. A process for the preparation of 2,2,4,4-tetramethylcyclobutane-1,3-diol, comprising:
(A) continuously feeding to a hydrogenation zone hydrogen and a hydrogenatable reactant comprising 2,2,4,4-tetramethylcyclobutane-1,3-dione at a hydrogen: 2,2,4,4-tetramethylcyclobutane-1,3-dione molar ratio of about 100:1 to about 500:1, wherein the hydrogen and hydrogenatable reactant are in the gas phase;
(B) continuously contacting the hydrogen and hydrogenatable reactant of step (A) at a temperature of about 100 to about 160° C. and a pressure of about 14 to about 21 bars with a catalyst comprising about 1 to about 8 weight percent ruthenium, based on the total weight of the catalyst, deposited on a support comprising activated carbon, carbonized phenol formaldehyde resin particles, carbonized polysulfonated vinylaromatic polymer particles, graphitized carbon, or combinations thereof, to form a hydrogenation product comprising 2,2,4,4-tetramethylcyclobutane-1,3-diol having a cis:trans ratio of about 1:1 to about 1.6:1, wherein the temperature is greater than the dew point of the hydrogenation product; and
(C) continuously recovering from the hydrogenation zone a gaseous effluent comprising the hydrogenation product.

18. The process according to claim 17 wherein the hydrogenatable reactant further comprises at least one non-protic solvent.

\* \* \* \* \*